United States Patent
Wilson et al.

(10) Patent No.: US 10,583,211 B2
(45) Date of Patent: Mar. 10, 2020

(54) RADIOACTIVE COMPOSITIONS AND METHODS FOR THEIR THERAPEUTIC USE

(71) Applicant: IsoTherapeutics Group LLC, Angleton, TX (US)

(72) Inventors: David A Wilson, Lake Jackson, TX (US); R. Keith Frank, Lake Jackson, TX (US); Jaime Simon, Angleton, TX (US); Druce K Crump, Lake Jackson, TX (US)

(73) Assignee: IsoTherapeutics Group LLC, Angleton, TX (US)

( * ) Notice: Subject to any disclaimer, the term of this patent is extended or adjusted under 35 U.S.C. 154(b) by 181 days.

(21) Appl. No.: 15/600,184

(22) Filed: May 19, 2017

(65) Prior Publication Data

US 2017/0258949 A1 Sep. 14, 2017

Related U.S. Application Data

(62) Division of application No. 14/367,758, filed as application No. PCT/US2012/071256 on Dec. 21, 2012, now Pat. No. 9,687,574.

(60) Provisional application No. 61/606,734, filed on Mar. 5, 2012, provisional application No. 61/578,630, filed on Dec. 21, 2011.

(51) Int. Cl.
*A61K 51/00* (2006.01)
*A61M 36/14* (2006.01)
*A61K 51/12* (2006.01)

(52) U.S. Cl.
CPC ...... *A61K 51/1282* (2013.01); *A61K 51/1244* (2013.01); *A61K 51/00* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 4,533,541 A | 8/1985 | Srivastava et al. | |
| 4,906,450 A | 3/1990 | Lieberman et al. | |
| 5,045,289 A | 9/1991 | Fernando et al. | |
| 5,061,476 A | 10/1991 | Simon et al. | |
| 5,853,695 A | 12/1998 | Srivastava et al. | |
| 6,004,532 A | 12/1999 | Srivastava et al. | |
| 6,132,642 A | 10/2000 | Kane | |
| 6,231,832 B1 | 5/2001 | Srivastava et al. | |
| 6,503,477 B1 | 1/2003 | Srivastava et al. | |
| 7,045,166 B2 | 5/2006 | Simon et al. | |
| 7,731,648 B2 | 6/2010 | Ivkov | |
| 9,687,574 B2 * | 6/2017 | Wilson | A61K 51/1244 |
| 2006/0014938 A1 | 1/2006 | Groman | |
| 2010/0092576 A1 | 4/2010 | Hallenbeck et al. | |
| 2011/0165070 A1 | 7/2011 | Stephens et al. | |
| 2012/0316633 A1 * | 12/2012 | Flanagan | A61F 2/82 623/1.11 |

OTHER PUBLICATIONS

Atkins et al, J. Nucl. Med. 36, 725-729 (1995).
Krishnamurthy et al, J. Nucl. Med. 38, 230-237 (1997).
Srivastava et al, Clin. Cancer Res. 4, 61-68 (1998).

* cited by examiner

*Primary Examiner* — Michael G. Hartley
*Assistant Examiner* — Melissa J Perreira
(74) *Attorney, Agent, or Firm* — Technology Law PLLC; Karen L. Kimble

(57) ABSTRACT

This invention concerns a pharmaceutically-acceptable composition of radioactive metals, which are used for treating various diseases in animals or humans, such as cancer and arthritis.

11 Claims, No Drawings

RADIOACTIVE COMPOSITIONS AND METHODS FOR THEIR THERAPEUTIC USE

CROSS REFERENCE TO RELATED APPLICATIONS

This application is a divisional application from the U.S. application Ser. No. 14/367,758, filed (pending), as a national phase application under 371 from internation application PCT/US2012/071256, filed 21 Dec. 2012 (inactive), which claims benefit of two US provisional applications 61/578,630, filed Dec. 21, 2011 and 61/606,734, filed Mar. 5, 2012 (both inactive).

FIELD OF THE INVENTION

The present invention concerns radioactive compositions when used for the therapeutic treatment of various diseases, such as treatment of undesirable tissue masses, for example bone cancer or soft tissue tumors, in mammals and humans by administration of a radioisotope composition directly to locations into or near a non-intracavitary area of the undesired tissue mass, i.e., via intratumural, intramedullary or intraosseous injection, or treatment of arthritis by injection into the synovial cavity.

BACKGROUND OF THE INVENTION

The treatment of various diseases using radioisotopes has been of concern for many years with various attempts to have effective treatment to prolong the quality of life of the mammal or human. Various compositions have been tried previously for this purpose with varying degrees of success. Some of these attempts are discussed below.

Bone Cancer

According to the American Academy of Orthopaedic Surgeons, "More than 1.2 million new cancer cases are diagnosed each year [in the US], and approximately 50 percent of these tumors can spread or metastasize to the skeleton." Metastatic bone cancer therefore afflicts over 500,000 patients in the US alone. Bone is the third most common site of metastatic disease. Cancers most likely to metastasize to bone include breast, lung, prostate, thyroid and kidney. In many cases there are multiple bone metastatic sites making treatment more difficult. Pain, pathological fractures and hypercalcemia are the major source of morbidity associated with bone metastasis. Pain is the most common symptom found in 70% of patients.

Primary bone cancer is much less prevalent (2,370 new cases and 1,330 deaths estimated in the US for 2007), but it is much more aggressive. This type of cancer is more likely to occur in young patients.

In contrast to humans, primary bone cancer is more prevalent in dogs than metastatic bone cancer. Large dogs frequently present with primary bone cancer.

Because of the aggressive nature of the disease, primary bone cancer in humans and animals is often treated by amputation of the area affected to prevent the cancer from spreading. In addition, chemotherapeutic agents are then used to decrease the chance of metastatic disease, especially to the lungs.

The pain associated with bone cancer, especially metastatic bone cancer, is often treated with narcotics. However, the patients have need for increasing amounts of narcotics to control the pain. The deleterious side effects of the narcotics result in a significant decrease in the patient's quality of life.

Another method for treatment is external beam radiation or more recently stereotactic radiotherapy of bone metastatic sites. However, current treatments with high energy electromagnetic radiation do not exclusively deliver radiation to the tumor. This treatment results in the necessity to administer the dose over about a week and has the difficultly of giving high doses of radiation to a tumor without having significant damage resulting to surrounding tissue.

Intraoperative Radiation Therapy (IORT) has permitted localized tumor destruction, but this procedure is expensive and associated with significant trauma due to surgery.

The ability to target bone tumors has been exploited in the field of radiopharmaceuticals for many years. Both diagnostic and therapeutic radiopharmaceuticals capable of targeting bone tumors generally use phosphonic acid functionality as the targeting moiety. For example, pyrophosphates have been used to deliver Tc-99m, a gamma-emitting diagnostic radioisotope, to bone. This technology was displaced by the bisphosphonates because of their increased stability in vivo. In addition, therapeutic radiopharmaceuticals for bone tumors were developed in the 1980's and 1990's. Of these, a series of chelates based on aminomethylene-phosphonic acids offer another type of functionality useful for targeting bone tumors. Thus ethylenediaminetetramethylenephosphonic acid (EDTMP) has been shown to be a very good chelating agent for delivering metals such as Sm, Gd, Ho, and Y to the bone.

Two radiopharmaceuticals, both based on radioactive metals, are marketed in the United States for the treatment of bone metastases. Metastron® (trademark of GE Healthcare Ltd.) is an injectable solution of strontium-89 (Sr-89) given as its chloride salt. Quadramet® (trademark of EUSA Pharma) is a phosphonic acid (EDTMP) chelate of samarium-153 (Sm-153). Both of these agents concentrate in normal bone as well as in the metastatic lesions. This gives a radiation dose to the bone marrow resulting in a temporary but significant suppression of the immune system. For that reason these agents are contraindicated when chemotherapeutic agents are planned as a part of the patient's treatment. Thus a patient may suffer from bone pain while waiting to receive a chemotherapeutic regimen for the primary cancer.

When these available chelates are injected intravenously, about 50% of the injected dose concentrates in the bone. The rest is efficiently cleared by the kidneys and into the bladder; however, because of this clearance, toxicity to these organs has been observed when administering large therapeutic doses of bone seeking radiopharmaceuticals. Although the chelate concentration in the site of a bone tumor is as much as 20 times that of normal bone, significant amounts of radioactivity are taken up by normal bone. In addition, only a small fraction of the radiation dose is associated with the tumor. Because of the fast kidney clearance and uptake in normal bone, only about 0.1% of the dose goes to the site of the tumor. Administration of larger doses of bone agents is limited by the dose to the bone marrow.

An example of the bisphosphonate chelant, methylenediphosphonic acid (MDP), is shown in the structure below.

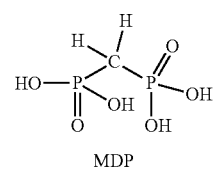

MDP

Two aminomethylenephosphonic acid chelants, ethylenediaminetetra-methylenephosphonic acid (EDTMP) and 1,4,7,10-tetraazacyclododecane-1,4,7,10-tetra(methylenephosphonic acid) (DOTMP), are shown in the structures below.

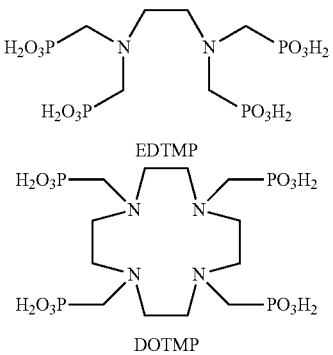

EDTMP

DOTMP

To date even combinations of treatments have not been effective at resolving bone tumors. Thus it is still common practice to amputate a limb to stop the spread of bone cancers. In the case of metastatic bone cancer, pain palliation and maintaining quality of life is often the goal in contrast to resolution of the tumors. There clearly is a need for more effective therapy to treat bone cancer.

Stannic (Sn(IV)-117m) chelates have been taught for the palliation of pain from bony metastases and for the treatment and regression of bone cancer by localization of a portion of the radioactive dose in the skeletal system after intravenous injection or infusion. Sn(IV)-117m decays with the emission of abundant conversion electrons of specific energy of 127-129 keV and 152 keV with a half-life of approximately 14 days. These conversion electrons have a range sufficient for irradiating bone tumors, while imparting a smaller dose to the bone marrow versus beta emitting radionuclides. Sn(IV)-117m also possesses an ideal 160 keV gamma emission and can be easily detected and imaged using conventional gamma detectors and thus enables one to monitor the in vivo biodistribution of the isotope.

Srivastava et al. (U.S. Pat. Nos. 4,533,541 and 5,853,695) teach Sn(IV)-117m chelates of methylenediphosphonate (MDP), pyrophosphate (PYP), ethylidenehydroxy disodium phosphonate (EHDP), and diethylenetriaminepentaacetic acid (DTPA) as being capable of localizing in the skeletal system after intravenous injection or infusion.

Srivastava et al. (U.S. Pat. Nos. 6,231,832 and 6,503,477) teach Sn(IV)-117m chelates of polyhydroxycarboxylates, such as oxalates, tartrates, citrates, malonates, gluconates, and glucoheptonates as being capable of localizing in the skeletal system after intravenous injection or infusion.

Srivastava et al. (U.S. Pat. No. 6,004,532) teach the use of the Sn(IV)-117m chelate of DTPA for palliation of bone pain associated with cancer and for the treatment of osseous tumors after intravenous injection or infusion.

Atkins, et al., *J. Nucl. Med.* 36, 725-729 (1995), and Krishnamurthy, et al., *J. Nucl. Med.* 38, 230-237 (1997), each report on phase (II) studies using the Sn(IV)-117m DTPA chelate for pain palliation after intravenous injection of the Sn(IV)-117m DTPA formulations.

Srivastava et al., *Clin. Cancer Res.* 4, 61-68 (1998), report on the use of Sn(IV)-117m DTPA in a phase I/II clinical study for the treatment of metastatic bone pain.

Clearly, there is still a need for a more effective therapy to treat bone pain and bone cancer.

Brachytherapy

In contrast to external beam radiotherapy, where an external beam of radiation is directed to the treatment area, brachytherapy is a form of radiotherapy where a radioactive source is placed inside or next to the area requiring treatment. Conventional brachytherapy is sometimes referred to as sealed source radiotherapy or endocurietherapy and is commonly used to treat localized prostate cancer and cancers of the head and neck. Superficial tumors can be treated by placing sources close to the skin. Interstitial brachytherapy is where the radioactive source is inserted into tissue. Intracavitary brachytherapy involves placing the source in a pre-existing body cavity. Intravascular brachytherapy places a catheter with the source inside blood vessels.

In most of these cases the radioactive material is sealed or encapsulated in a metal casing. Because of this casing, most of the radioactive sources are electromagnetic radiation (i.e., X-rays and gamma photons) emitting radionuclides such that the radiation can penetrate the outer casing and deliver a radiation dose to surrounding tissue. Administration of the radioisotope without this encapsulation may result in migration of the radioisotope to other areas of the body, which may create side effects in the patient. Particle emitting radionuclides such as beta (β) and alpha (α) emitters are rarely used in this method because a significant portion of the dose would not penetrate such metal casing. However, in many instances the gamma photons penetrate beyond the desired treatment area, which results in significant side effects. Therefore, a more specific method to deliver radiation is needed.

The prostate is a gland in the male reproductive system located just below the urinary bladder and in front of the rectum. It is about the size of a walnut and surrounds the urethra. In 2007 the American Cancer Society estimated 218,890 new cases and 27,050 deaths due to prostate cancer in the US. Treatment options include surgery, external radiation therapy, and brachytherapy. In many cases brachytherapy is the preferred choice due to fewer traumas to surrounding tissues. However since the radioisotopes selected for this application are gamma (γ) emitters, the problem of delivering an undesired radiation dose to surrounding tissue remains.

The radioactive sources used for conventional brachytherapy are sealed, for example, in "seeds," wires, or encapsulated in a metal casing and are referred to as a sealed radioactive source. Conversely, a non-sealed radioactive source is one that is not sealed, for example, in seeds, wires, or encapsulated in a metal casing. Permanent prostate brachytherapy involves implanting between 60 and 120 rice-sized radioactive seeds into the prostate. One type of radioactive seed is based on I-125 which has a 59.4 day half-life and emits multiple X-rays around 30 keV. Recently a shorter half-life alternative has been proposed with Cs-131 which has a 9.7 day half-life and emits X-rays of about 30 keV. Alternatively, Pd-103 is used which has a 17 day half-life and emits X-rays of about 20 keV. Another option is Ir-192 which has a half-life of 73.8 days and gamma emissions at 468 keV. Ir-192 can be used to give different doses to different parts of the prostate. All these isotopes emit electromagnetic radiation that penetrates beyond the prostate and into normal tissue causing problems such as impotence, urinary problems, and bowel problems. Although in most cases the seeds stay in place, seed migration does occur in a portion of patients, usually to the urethra or bladder.

In some cases, brachytherapy is used to destroy cancer cells left over after a surgical procedure. For example, breast cancer patients can be treated with a technology by the name of MammoSite® Radiation Therapy System (trademark of Hologic, Inc.). This involves a balloon catheter that is inserted into the area of the breast where a tumor was removed. The balloon is expanded and radiation is delivered via a small bead attached to a wire. Similarly, the space surrounding a resected brain tumor can be treated using a balloon catheter inflated with a radioactive solution of I-125. This technology is called GliaSite® Radiation Therapy System (e.g., trademark of Cytyc Corp.; U.S. Pat. No. 6,315,979). In these cases the balloon prevents the radioactivity from going systemic. Again, the radioisotopes used are those emitting penetrating electromagnetic radiation (i.e., X-rays or gamma rays).

Beta emitting radioisotopes are being used in what could be categorized as brachytherapy. For example, liver cancer has been treated with a form of brachytherapy. This technology called Selective Internal Radiation Therapy (SIRT) delivers radioactive particles to a tumor via the blood supply. The radioactive particles are positioned via a catheter in the hepatic artery, the portal vein, or a branch of either of these vessels. The catheter is guided to the branch of the blood vessel that feeds the tumor, and then the microspheres are infused. The radioactive microspheres become trapped in the capillary beds of the tumor and the surrounding tissues, which method results in a more targeted radiation dose to the tumor. There are currently two products that take this approach, both are microspheres labeled with Y-90, TheraSphere® (trademark of MDS Nordion, Inc.), and SIR-Spheres® (trademark of SIRTeX® Medical). TheraSpheres are glass microspheres which have a diameter of 25±10 μm so they are trapped mainly within tumor terminal arterioles, which are estimated to have a diameter of 8-10 μm. SIR-Spheres are resin-based microspheres that are approximately 32 μm in diameter. One concern with both of these products is that a portion of the radioactive microspheres can migrate to other tissues such as the lungs and cause undesired side effects.

Ho-166 bound to chitosan has also been proposed to treat cancer cells. Thus *J. Nucl. Med.* 39(12), 2161-6 (1998 December) describes a method to treat liver cancer by administering this compound via the hepatic artery. However, "shunting" of radioactivity to the lung has again been a problem. In addition, it is a cumbersome technique to determine the blood supply to the tumor and to deliver the particles in the selected blood vessels.

Kyker et al., *Federation Proc.* 13, 245-246 (1954), Lewin, et al., *J. Nat. Cancer Inst.* 15, 131-143 (1954), and Andrews et al., *International Conference on the Peaceful Uses of Atomic Energy*, 10, 122 (1956), describe attempts to treat cancer by forming radioactive colloids in situ in the body but with limited success.

Hyperthermia

Hyperthermia is a procedure where the temperature of a targeted part of the body is raised in order to destroy cancer cells. Usually temperatures in the approximate range of 42-46° C. are employed. Iron oxide magnetic particles have been used to obtain such a temperature range by the action of an externally applied magnetic field. The benefit that the magnetic iron oxide particles bring is that the heating step can be localized at the site of the tumor(s). It has been reported that the "heating potential" of the particles is strongly dependent on the size and shape of the particles so these parameters must be optimized. A particle size in the range of 10 to 50 nm is frequently used. Eileen Gribouski and Rafael Jaimes (*The Use of Iron-oxide Nanoparticles for Hyperthermia Cancer Treatment and Simultaneous MRI Monitoring—A major Qualifying Project Submitted to the Faculty Of Worcester Polytechnic Institute, Apr.* 30, 2009) have indicated that an effective tumor treatment involves "magnetic embolization hyperthermia" wherein magnetic iron oxide particles are injected directly to the site of treatment. When the particles are exposed to an AC magnetic field, they absorb energy and increase the temperature in the area of the magnetic particles. This technique is effective due to its high selectivity. It has been reported that the hyperthermia process needs to be administered together with other cancer treatments [e.g., Pedro Tartaj et al., "The Preparation of Magnetic Nanoparticles for Applications in Biomedicine," *J. Phys. D: Appl. Phys.*, 36, R182-R197 (2003)].

Arthritis

Rheumatoid arthritis is a prevalent disease characterized by chronic inflammation of the synovial membrane lining the afflicted joint. It is also classified as an autoimmune disease. Multiple joints are often involved with rheumatoid arthritis. Current treatment methods for severe cases of rheumatoid arthritis include the removal of the synovial membrane, e.g., synovectomy. Surgical synovectomy has many limitations including the risk of the surgical procedure itself and the fact that a surgeon often cannot remove all of the membrane. The diseased tissue remaining may eventually regenerate, causing the same symptoms which the surgery was meant to alleviate.

Radiation synovectomy is radiation-induced ablation of diseased synovial membrane tissue accomplished by injecting a radioactive compound into the diseased synovium. Early attempts to perform radiation synovectomy were hampered by instability of the radioactive compositions utilized and by leakage of such compounds from the synovium into surrounding healthy tissues. The instability of labile radionuclide-complexes resulted in release of the radionuclide from the colloid complex and retention of the radionuclide in surrounding soft tissues. Significant leakage of the radioactive compound from the site of injection exposed normal tissues to dangerous levels or radiation. Because of these limitations, new radiolabeled compositions were sought which would have minimal leakage.

Deutch et al. (WO9105570 A1) teach the use of Re-188 or Re-186 attached to albumin microspheres, sulfur colloids, or glass beads; Simon et al. teach the use of rare earth isotopes such as Sm-153, Ho-166, Y-90, and Lu-177 adsorbed on a previously prepared particle (U.S. Pat. No. 5,300,281); Day et al. (U.S. Pat. No. 4,889,707) teach the use of a biodegradable glass material containing a beta radiation emitting radioisotope; Brodack et al. (U.S. Pat. No. 5,320,824) teach particles that are attached to various radionuclides, and also teach that small colloidal particles of hydroxy apatite can aggregate into non-colloidal particles and have utility for the treatment of arthritis; and Brodack, et al. (WO9701304 A1) teach the use of paramagnetic particles containing therapeutic radionuclides.

Srivastava et al. (U.S. Pat. Nos. 6,231,832 B1 & 6,503,477 B1) teach the use of different $Sn(Sn^{4+})$-117m chelates for the treatment of pain resulting from various bone/joint disorders including rheumatoid arthritis and osteoarthritis. Preferred chelating agents include polyhydroxycarboxylates such as oxalates, tartrates, citrates, malonates, gluconates and glucoheptonates.

Liberman et al. (U.S. Pat. No. 4,906,450) teach the use of the radionuclide Sn(II)-121 hydroxide in a carrier of ferric hydroxide macroaggregate. In contrast to Sn(IV)-117m, Sn-121 does not possess gamma photons and is not easily detected and imaged using conventional gamma detectors.

U.S. Pat. Nos. 4,752,464; 4,849,209 and 3,906,450 describe compositions comprising a radioactive colloid in which a radionuclide is entrapped within an iron hydroxide matrix. The radioactive colloids are useful in radiation ablation procedures, for example, ablation of a diseased synovium in rheumatoid arthritis. However, the use of radioactive colloids may still result in significant leakage of radioactivity from the site of injection, e.g., a synovium, and into the surrounding normal tissues, exposing normal tissues to an undesirable amount of radiation. To compensate for the leakage, a radioactive metal having a short half-life, such as dysprosium-165 (Dy-165) with a half-life of 2.3 hours, has been proposed for use as the therapeutic radionuclide. Because of its short half-life, the majority of Dy-165 radioactivity decays before significant leakage can occur, thereby minimizing the dose of radiation to normal tissues.

However, the use of radioactive metals having a short half-life severely limits the utility of the therapeutic radiation procedure in two significant ways. First, radioactive compositions prepared with short half-life isotopes lose a significant amount of radioactivity because of decay during shipment to distant locations. Second, to achieve a therapeutic dose of a composition containing a radioactive metal having a short half-life, large amounts of radioactive materials must be used. As a result, clinical personnel must handle large amounts of radioactive materials, which pose safety issues for repeated exposure to these personnel.

Osteoarthritis is the most common type of arthritis and is caused by the breakdown of joint cartilage. The loss of cartilage and the subsequent bone rubbing on bone is quite painful. Osteoarthritis usually starts in a single joint. Treatment of osteoarthritis focusses on pain relief. Nonsteroidal, anti-inflammatory drugs (NSAIDs), cortisone and hyaluronic acid injections, massage, and other treatments are usually used in an attempt to control the pain. Inflammation in the synovium membrane can be an important factor in individuals with osteoarthritis. Dimitrios Chatzopoulos, et al. [*Nuclear Medicine Communications*, 30(6), 472-479 (2009)] report that the use of Y-90 synovectomy exerts a beneficial therapeutic effect for a substantial number of patients with osteoarthritis knee pain and synovial inflammation and believe that radiation synovectomy is an option for treating osteoarthritis.

As is evident from the discussion above, better technology to ablate undesirable cells in various diseases is needed. In the general field of brachytherapy and arthritis, more effective methods of delivering radioisotopes to tumors and arthritic sites are needed that give a radiation dose specifically to the treatment area with little to no dose to non-target tissues. Clearly, such an improved technology is desirable to treat these various diseases in humans and animals.

SUMMARY OF THE INVENTION

This invention provides a Non-Sealed radioactive pharmaceutically-acceptable composition represented by Formula (I) below.

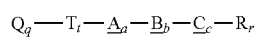

Formula (I)

wherein:

Q is a Substrate of a different material from $\underline{A}_a$-$\underline{B}_b$-$\underline{C}_c$ entity, wherein such Substrate has the $\underline{A}_a$-$\underline{B}_b$-$\underline{C}_c$ entity deposited or adhered thereto; and is an injectable or implantable Substrate that is either pharmaceutically-acceptable or can be Coated to be pharmaceutically-acceptable;

q is equal to 1 or 0, wherein 1 means the entity is present and 0 means the entity is not present;

T is a non-radioactive iron hydroxide, iron oxide, gadolinium hydroxide or gadolinium oxide;

t is equal to 1 or 0, wherein 1 means the entity is present and 0 means the entity is not present;

$\underline{A}$ is $J_v M^*_w(OH)_x(CO_3)_y(AN)_z \cdot nH_2O$, wherein:
  J is a lanthanide metal ion capable of forming hydroxy carbonate compounds;
  v is greater than or equal to 0;
  M* is radioactive Sm-153, Ho-166, Y-90, or Lu-177 or mixtures thereof, wherein their respective non-radioactive Rare-earth Type Metal is usually present;
  w, x and y are each independently greater than 0;
  AN is a pharmaceutically-acceptable anionic moiety; and
  z and n are each independently greater than or equal to 0;

a is equal to 1 or 0, wherein 1 means the entity is present and 0 means the entity is not present;

$\underline{B}$ is $M^*_w(OH)_x(CO_3)_y \cdot nH_2O$, wherein:
  M* is radioactive Sm-153, Ho-166, Y-90, or Lu-177 or mixtures thereof, wherein their respective non-radioactive Rare-earth Type Metal is usually present;
  w, x and y are each independently greater than 0; and
  n is greater than or equal to 0;

b is equal to 1 or 0, wherein 1 means the entity is present and 0 means the entity is not present;

$\underline{C}$ is $Sn(L)_u$-$\{M_w(OH)_x(CO_3)_y \cdot nH_2O\}_p$, wherein:
  Sn is radioactive tin (IV)-117m but also contains non-radioactive tin isotopes;
  L is hydrous oxide, hydroxide, or oxyhydroxide such that $Sn(L)_u$ is hydrous stannic oxide, stannic hydroxide, or stannic oxyhydroxide, or mixtures thereof;
  u is greater than 0;
  M is a Rare-earth Type Metal, or mixture thereof, wherein M can further include a radioactive Rare-earth Type Metal selected from the group consisting of Y-90, Sm-153, Ho-166, or Lu-177, or mixtures thereof;
  w, x and y are each independently greater than 0;
  n is greater than or equal to 0; and
  p is equal to 1 or 0, wherein 1 means the entity is present and 0 means the entity is not present;

c is equal to 1 or 0, wherein 1 means the entity is present and 0 means the entity is not present;

R is a Coat comprising a substance of a different composition than $\underline{A}_a$-$\underline{B}_b$-$\underline{C}_c$ entity, which covers $\underline{A}$-$\underline{B}_b$-$\underline{C}_c$, and if q is 1, also Coats Substrate Q, and the resulting Coated composition is pharmaceutically-acceptable for injection; and r is equal to 1 or 0, wherein 1 means the entity is present and 0 means the entity is not present;

with the provisos that one and only one of a, b and c are equal to 1, the others being equal to 0 (i.e. one and only one of $\underline{A}$, $\underline{B}$, or $\underline{CC}$ is present); if either q or t is equal to 1, then the other is equal to 0 (i.e. only one of Q or T may optionally be present); each of u, v, w, x, y and z are of a numeric value, fractional values included, such that electrical neutrality is attained; and n is greater than or equal to 0 to provide optional water of hydration.

The formulated, pharmaceutically-acceptable compositions of Formula (I) can be colloids, suspensions or slurries, which are usually formulated as pharmaceutically-acceptable liquids, such as in water or saline, for injection into an animal or human in need of such treatment. Such formulations may also have present one or more pharmaceutically-acceptable carriers, excipients, diluents, suspension aids, preservatives, crystal growth modifiers or buffers. However, if the composition has Q present (e.g. a stent), it can be useful for implantation.

This invention provides Non-Sealed radioactive pharmaceutically-acceptable compositions as defined by Formula (I), and its use in therapeutic methods for various diseases. The formulated radioactive composition of Formula (I) can deliver relatively large radiation doses from a Non-Sealed radioactive source to the site of diseased cells, such as an undesired tissue mass, including infections and cancerous tumors in both soft tissue and bone, and arthritis for the purpose of ablating said undesirable tissue. Also this invention minimizes the amount of radiation dose to non-target tissues in order to minimize side effects.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

Coat means a layer of one substance covering another

CT means computed tomography, usually X-ray computed tomography hr means hours

Hydroxy Carbonate Entity means $M_w(OH)_x(CO_3)_y \cdot nH_2O$ as defined in Formula (IV) and Formula (V)

Intracavitary means inside a pre-existing body cavity such as sinus or peritoneal mCi means milliCuries μCi means microCuries μL means microliters min means minutes MRI means magnetic resonance imaging MURR means University of Missouri Research Reactor Non-intracavitary means not in a pre-existing body cavity such as sinus or peritoneal Non-Sealed means a source that is not encapsulated, for example, in "seeds" or wires, or in a metal casing PET means positron emission tomography Rare-earth Type Metals means Sm, Ho, Lu, and Y Radioactive Hydroxy Carbonate means the $J_vM^*_w(OH)_x(CO_3)_y(AN)_z \cdot nH_2O$ entity as defined by A in Formula (I) and in Formula (II)

Radioactive Sn Entity means $Sn(L)_u\{M_w(OH)_x(CO_3)_y \cdot nH_2O\}_p$ as defined by C in Formula (I), Formula (IV), and Formula (V), and Sn means radioactive tin(IV)-117m which also contains non-radioactive Sn isotopes sec means seconds Substrate means a surface upon which a different material is deposited or adhered Composition This invention provides a Non-Sealed radioactive pharmaceutically-acceptable composition represented by Formula (I) below.

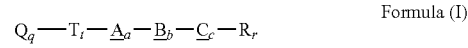

Formula (I)

wherein:

Q is a Substrate of a different material versus the $\underline{A}_a$-$\underline{B}_b$-$\underline{C}_c$ entity, wherein such Substrate has the $\underline{A}_a$-$\underline{B}_b$-$\underline{C}_c$ entity deposited or adhered thereto; and is an injectable or implantable Substrate that is either pharmaceutically-acceptable or can be Coated to be pharmaceutically-acceptable, examples of Q include but are not limited to alumina, silica, barium titanate, metal oxides and hydroxides (such as iron oxide, iron hydroxide, titanium dioxide, gadolinium hydroxide, and yttrium oxide), polystyrene latex, hydroxyapatite [e.g. $Ca_5(PO_4)_3OH$], and magnetic particles including magnetite ($Fe_3O_4$), maghemite (gamma $Fe_2O_3$), and hematite (alpha $Fe_2O_3$), polystyrene-polymethacrylate copolymers, poly(lactic acid) particles, DL-lactide/glycolide copolymers, stents, shunts, and various derivatives of the particles containing surface modifications such as —COOH, alkyl-OH, acrylate, $SiO_2$, and polyethyleneglycol (PEG);

T is non-radioactive iron and/or gadolinium hydroxide and/or oxide;

$\underline{A}$ is $J_vM^*_w(OH)_x(CO_3)_y(AN)_z \cdot nH_2O$ $\underline{B}$ is $M^*_w(OH)_x(CO_3)_y \cdot nH_2O$ $\underline{C}$ is $Sn(L)_u\{M_w(OH)_x(CO_3)_y \cdot nH_2O\}_p$ R is a Coat comprising a substance of a different composition than the $\underline{A}_a$-$\underline{B}_b$-$\underline{C}_c$ which covers $\underline{A}_a$-$\underline{B}_b$-$\underline{C}_c$, and if q is 1, also Coats Substrate Q, and the resulting Coated composition is pharmaceutically-acceptable for injection, examples of such Coatings include but are not limited to poly(lactic acid) and DL-lactide/glycolide copolymers, polyethylene glycol (PEG), hydroxyapatite, and various organic or inorganic polymers and derivatives;

J is a lanthanide metal ion capable of forming hydroxy carbonate compounds, such as fluorescent gadolinium, europium, and erbium;

M* is radioactive Sm-153, Ho-166, Y-90, or Lu-177 or mixtures thereof, wherein their respective non-radioactive Rare-earth Type Metal is usually present;

M is a Rare-earth Type Metal, or mixture thereof, wherein M can further include a radioactive Rare-earth Type Metal selected from the group consisting of Y-90, Sm-153, Ho-166, or Lu-177, or mixtures thereof;

AN is a pharmaceutically-acceptable anionic moiety, examples include but are not limited to nitrate, chloride, hydrogen phosphate, dihydrogen phosphate, fluoride, sulfate and oxalate;

Sn is radioactive tin (IV)-117m but also contains non-radioactive Sn isotopes;

L is hydrous oxide, hydroxide, or oxyhydroxide such that $Sn(L)_u$ is hydrous stannic oxide, stannic hydroxide, or stannic oxyhydroxide, or mixtures thereof;

q, t, a, b, c, r and p are equal to 1 or 0, wherein 1 means the entity is present and 0 means the entity is not present;

w, x, y and u are greater than 0;

v, z and n are greater than or equal to 0;

with the proviso that one and only one of a, b and c are equal to 1, the others being equal to 0 (i.e. one and only one of A, B, or C must be present); if either q or t is equal to 1 then the other is equal to 0 (i.e. only one of Q or T may optionally be present); each of u, v, w, x, y and z are of a numeric value, fractional values included, such that electrical neutrality is attained; and n is greater than or equal to 0 to provide optional water of hydration.

This invention provides Non-Sealed radioactive pharmaceutically-acceptable compositions as defined by Formula (I), and therapeutic methods for various diseases that can deliver relatively large radiation doses from a Non-Sealed radioactive source to the site of diseased cells, such as an undesired tissue mass, including infections and cancerous tumors in both soft tissue and bone, and arthritis for the purpose of killing said undesirable tissue. Also this invention minimizes the amount of radiation dose to non-target tissues in order to minimize side effects. These properties provide advantages over the discussed art.

One aspect of this invention provides a Non-Sealed radioactive pharmaceutically-acceptable composition, comprising a metal hydroxy carbonate composition wherein the radioactive metal in the hydroxy carbonate compound is yttrium-90, samarium-153, holmium-166, or lutetium-177, or mixtures thereof, wherein the respective non-radioactive metal hydroxy carbonate usually is present, and derivatives and/or modifications thereof as defined by Formula (II) below.

More specifically, this invention provides a pharmaceutically-acceptable composition of Formula (I) wherein a is equal to 1 and t, b and c are equal to 0 (i.e. $Q_q\text{-}\underline{A}\text{-}R_r$) which is represented by Formula (II) below.

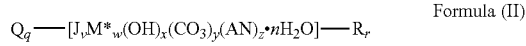

Formula (II)

wherein:

Q, J, M*, AN, R, q, v, w, x, y, z and n are as defined in Formula (I)

Another aspect of this invention provides Non-Sealed co-precipitated radioactive pharmaceutically-acceptable aggregate compositions, comprising a radioactive metal hydroxy carbonate composition as defined by Formula (III) below.

More specifically, this invention provides a pharmaceutically-acceptable composition of Formula (I) wherein t and b are both equal to 1; and q, a, c and r are all equal to 0 (i.e. T-B) which is represented by Formula (III) below.

Formula (III)

wherein:

T, M*, w, x, y, and n are as defined in Formula (I).

Another aspect of this invention provides Non-Sealed, radioactive, pharmaceutically-acceptable compositions, comprising Sn(IV)-117m as defined by Formula (IV) and Formula (V) below, and a therapeutic method for treating various diseases, where the present method can deliver relatively large radiation doses from such compositions to arthritic sites for the purpose of treating said arthritic sites and/or alleviating pain. Also this invention minimizes the amount of radiation dose to non-target tissues in order to minimize side effects.

Another aspect of this invention provides a Non-Sealed radioactive pharmaceutically-acceptable composition, comprising a radioactive Sn(IV)-117m composition as defined by Formula (IV) below.

More specifically, this invention provides a pharmaceutically-acceptable composition of Formula (I) wherein c is equal to 1; and t, a and b are each equal to 0 (i.e. $Q_q\text{-}\underline{C}\text{-}R_r$) which is represented by Formula (IV) below.

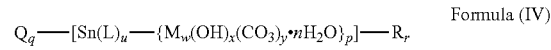

Formula (IV)

wherein:

Q, Sn, L, M, R, q, u, w, x, y, n, p and r are as defined in Formula (I).

Another aspect of this invention provides Non-Sealed co-precipitated radioactive pharmaceutically-acceptable aggregate compositions, comprising a radioactive Sn(IV)-117m composition as defined by Formula (V) below.

More specifically, this invention provides a pharmaceutically-acceptable composition of Formula (I) wherein t and c are both equal to 1; and q, a, b and r are all equal to 0 (i.e. T-C) which is represented by Formula (V) below.

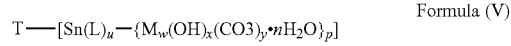

Formula (V)

wherein:

T, Sn, L, M, u, w, x, y, n and p are as defined in Formula (I).

The aqueous compositions of Formula (I), Formula (II), Formula (III), Formula (IV) and Formula (V) are colloids, suspensions or slurries, which are usually formulated as pharmaceutically-acceptable liquids, such as in water or saline, for injection that may also have present one or more pharmaceutically-acceptable carriers, excipients, diluents, suspension aids, preservatives, crystal growth modifiers or buffers. However, if the composition has Q present (e.g. a stent), it can be useful for implantation.

One aspect of this invention concerns a composition and a method for the therapeutic treatment of a Non-intracavitary, undesirable tissue mass or arthritis in an animal or human in need of such treatment. More specifically, this invention provides compositions of Formula (II) and Formula (III) comprising yttrium-90 hydroxy carbonate and/or samarium-153 hydroxy carbonate and/or holmium-166 hydroxy carbonate and/or lutetium-177 hydroxy carbonate particles, wherein the respective non-radioactive yttrium hydroxy carbonate and/or samarium hydroxy carbonate and/or holmium hydroxy carbonate and/or lutetium hydroxy carbonate is usually also present. Preferred combinations are: non-radioactive yttrium hydroxy carbonate present with radioactive yttrium-90 hydroxy carbonate; non-radioactive samarium hydroxy carbonate present with radioactive samarium-153 hydroxy carbonate; non-radioactive holmium hydroxy carbonate present with radioactive holmium-166 hydroxy carbonate; non-radioactive lutetium hydroxy carbonate present with radioactive lutetium-177 hydroxy carbonate; and certain modifications and derivatives thereof, in a pharmaceutically-acceptable, aqueous medium.

One method of this invention uses a therapeutically-effective quantity of the compositions of Formula (II) and Formula (III), administered in one or more locations into or near a Non-intracavitary, undesirable tissue mass (e.g. cancer) in an animal or human in need of such treatment. Another method of this invention uses a therapeutically-effective quantity of these hydroxy carbonates, administered in one or more locations into or near the synovial cavity to treat arthritis. In either method the treatment is such that a major portion of the dose remains at the site of injection (defined as greater than about 90% of the dose remaining at the site after two half-lives of the radioisotopes; more preferably greater than about 95% of the dose remaining at the site after 2 half-lives of the radioactive isotopes; and most preferably greater than about 98% of the dose remaining at the site after 2 half-lives of the radioisotopes) as determined by biolocalization data obtained by dissection of an animal (e.g. BALB/c mice or Sprague Dawley rats); wherein the values are corrected for radioactive decay. It is also important to recognize that deposition of radioactivity in non-target organs and tissues can impact the safety and efficacy of the treatment. Ideally, in mice, less than about 1% remaining in the carcass (including the contralateral femur) and less than about 0.2% in the liver plus the kidneys and, in rats, less than about 1% in the skeletal structure and less than about 0.2% in the liver plus the kidneys. In the case of mice (injection into the gastrocnemius muscle of the right hind leg is used as a model for Non-Intracavitary tumors), all tissues, including the whole carcass, and bedding were collected such that 100% of the radioactivity was accounted for. In the case of rats (injections were directly into the synovial cavity), the size of the animal precluded counting the entire carcass. Therefore samples of blood, muscle, and bone (contralateral femur) were collected and the total masses of those tissues were calculated. The tissue masses were calculated based on rat body weight using equations fitted to data in the literature [Henry H. Donaldson, *The Rat: Reference Tables and Data for the Albino Rat and the Norway Rat,* (1915)].

Administration of a therapeutically-effective dose is accomplished by the direct administration of a composition to the desired site. The radioactivity delivered to the site remains at the site of administration for a sufficient time to give a therapeutic radiation dose to that area. Compared with systemic administration approaches, the total amount of radioactivity administered is very small and the amount of radioisotope that leaches out of the treatment area is minimal; thus little to no radiation dose to normal tissues is realized.

Administration of the radioisotope composition can be via a microsyringe or another device capable of delivering small volumes of fluid such as a small pump. In one embodiment of the invention for treating bone tumors, a miniature drill is used to create one or more holes in a bone by which a catheter can be inserted through the holes and a device capable of delivering small volumes of fluid is used to deliver the dose. In other embodiments, a microsyringe can be used for the delivery of the dose.

Radioisotopes of this invention include particle-emitting isotopes that can deposit therapeutic amounts of ionizing radiation at the site of the undesired tissue mass.

Another aspect of this invention provides a Non-Sealed, radioactive, pharmaceutically-acceptable composition, comprising a Sn(IV)-117m composition as defined by Formula (IV) and Formula (V), and a therapeutic method for treating various diseases, where the present method can deliver relatively large radiation doses from such compositions to arthritic sites for the purpose of treating said arthritic sites and/or alleviating pain. Treatment of the mammal or human is accomplished using a therapeutically-effective quantity of the compositions of Formula (IV) and Formula (V), wherein the compositions are administered into or near the synovial cavity. Also this invention minimizes the amount of radiation dose to non-target tissues in order to minimize side effects.

More specifically, this invention comprises pharmaceutically-acceptable, Non-Sealed, radioactive Sn(IV)-117m compositions of Formula (IV) and the aggregate compositions of Formula (V):

One method of this invention uses a therapeutically-effective quantity of these Sn(IV)-117m compositions of Formula (IV) and Formula (V), administered in one or more locations into or near the synovial cavity to treat arthritis and/or alleviate pain. The treatment is such that a major portion of the dose remains at the site of injection (as defined earlier). Administration of a therapeutically-effective dose is accomplished by the direct administration of compositions of Formula (IV) and Formula (V) to the arthritic site. The radioactivity delivered remains at the site of administration for a sufficient time to give a therapeutic radiation dose to that area. Compared with systemic administration approaches, the total amount of radioactivity administered is very small and the amount of radioisotope that leaches out of the treatment area is minimal; thus little to no radiation dose to normal tissues is realized.

Method of Administration

Specifically, this invention involves the delivery of a therapeutically-effective amount of the pharmaceutically-acceptable, Non-Sealed formulated radioisotope compositions of Formula (II) and Formula (III) directly to the diseased cells, without systemic administration, such as to the synovial cavity or to an undesired tissue mass, including infections (e.g., osteomyelitis) and cancerous tumors, especially inoperable cancerous tumors, in both soft tissue and bone; such as cancerous tumors in bone, prostate, liver, lung, brain, muscle, breast, cervix and skin. Compositions of Formula (IV) and Formula (V) are administered specifically to the synovial cavity due to the ideal radiochemical properties of Sn-117m, including the ability to image in vivo.

Cancerous tumors treated in this invention are considered as occurring in Non-intracavitary body areas as this direct administration to the undesired tissue mass is directly into or very near such tissue mass and is not into any cavity. In contrast, the treatment of the synovium is by direct injection into the synovial cavity with compositions of Formula (II), Formula (III), Formula (IV) and Formula (V). The amount of radioactivity administered to the animal, including humans, of these compositions is effectively directed to the desired site and the administration is done where only the intended site is treated; not done by means that involve other body areas, e.g., no systemic administration (such as I.V.

administration). Non-target, normal tissue is spared exposure because only a very small amount of radioisotope is administered and the majority of the radioisotope mixture is immobilized at the administration site. Thus the majority of the radioactive decay of the isotope occurs at the site of injection with only small amounts of radioactivity leaching out of the injection site before a significant amount of the radioisotope decays. This results in a high radiation dose to the target area and extremely small doses to non-target tissues. The composition can be used to treat a variety of conditions of diseased cells where ablation is desired, particularly arthritis, cancerous tumors and other undesired tissue masses.

Radioisotopes used in Formula (II) and Formula (III) of this invention are particle emitters, preferably beta ($\beta$) emitters. Preferred radioisotopes are ions of rare-earth metals and yttrium including Sm, Ho, Lu, and Y. Sm, Ho, Lu, and Y have been referred to in the literature as "Rare-earth type metals" (e.g. U.S. Pat. No. 3,436,335). Preferred radioactive isotopes include: Sm-153, Ho-166, Y-90, and Lu-177 because they are isotopes with a relatively short half-life of less than about 7 days that also emit energetic beta particles: such criteria include Y-90 (half-life=64 hrs.), Ho-166 (half-life=26.8 hrs.), Sm-153 (half-life=46.7 hrs.) and Lu-177 (half-life=6.7 days). It is understood by those skilled in this area that often the radioisotopes contain their non-radioactive carrier isotopes as a mixture. The compositions Formula (IV) and Formula (V) containing Sn-117m (half-life=14 days) are limited for use in the treatment of arthritic sites.

Process and Derivatives

Hydroxy carbonates of non-radioactive metals such as the Rare-earth Type Metals have been prepared by different techniques that have been reported in the literature. For example, E. Zych, et al., *J. Alloys and Compounds*, 341, 385 (2002) prepared lutetium hydroxy carbonate by treating lutetium nitrate with ammonium bicarbonate and ammonia solution; whereas Tareen et al., *J. Cryst. Growth*, 50, 527 (1980) have used oxalic acid as a $CO_2$ source in a procedure to produce hydroxy carbonates of La, Nd, Sm, Eu, and Gd. One particularly effective process (homogeneous precipitation using urea) disclosed by Egon Matijevic (U.S. Pat. No. 5,015,452); Daniel Sordelet and Mufit Akinic, *J. of Colloid and Interface Sci.*, 122(1), 47-59, (1988); and Xianpeng Qin, *Materials Research Bulletin*, 46, 170-174 (2011), all describe a procedure for the synthesis of uniform hydroxy carbonate particles of Rare-earth Type Metals. For example, Matijevic (U.S. Pat. No. 5,015,452) prepared hydroxy carbonate particles of gadolinium (Gd), terbium (Tb), europium (Eu), and samarium (Sm) and measured the fluorescence emission spectra of the compounds.

Iron oxide particles coated with a non-radioactive yttrium oxide shell doped with a small amount of europium have been prepared by Zhi Ya Ma et al., *J. Mater. Chem.*,19, 4695-4700 (2009). Y. S. Ahn and M. H. Han, "Synthesis of Yttrium Iron Garnet Precursor Particles by Homogeneous Precipitation," *J. of Materials Sci.*, 31 4233-4240 (1996), have reported the use of the homogeneous precipitation method wherein a solution of iron nitrate, yttrium nitrate and urea with an initial pH of 2 was heated and reacted at 90° C. to produce a hydrated yttrium hydroxy carbonate.$Fe_2O_3$ product.

The homogeneous precipitation procedure uses rare-earth and yttrium salts and urea as the reactants in solvents such as water or alcohol/water mixtures. Heating the aqueous mix by techniques generally known in the literature results in the decomposition of the urea to yield ammonia and carbon dioxide in situ. Alternatively, the decomposition of the urea can be achieved enzymatically using urease at low temperatures, such as room temperature, and is well documented in the literature (Unuma et al., "Enzyme-mediated synthesis of ceramic materials," *Journal of the Ceramic Society of Japan*, 119(8), 623-630, 2011). The hydroxide and carbonate anions that are produced will form precipitating nuclei with the metal cations when present above an initial supersaturation point and the anions are consumed by the growth of the nuclei. This results in a separation of the nucleation and growth of the metal hydroxy carbonate species and leads to the formation of uniform particles. The reaction conditions employed can be advantageously chosen to alter the morphology and size of the particles that are formed [e.g. submicron (Matijevic—U.S. Pat. No. 5,015,452) to micron (M. J. Haron et al., "Preparation of Basic Yttrium Carbonate for Phosphate Removal," *Water Environment Research*, 69, 1047-51, July/August 1997)]. Aiken et al. [*J. Am. Ceram. Soc.*, 71 (10) 845-53 (1988)] have used the homogeneous precipitation method using urea to prepare monodispersed particles of yttrium hydroxy carbonate as well as a mixed yttrium/cerium product. The procedures and the teachings in the references cited for preparing non-radioactive rare-earth and yttrium hydroxy carbonate compounds are hereby incorporated by reference in their entirety.

In the majority of cases the hydroxy carbonates of the non-radioactive metals that are formed are intermediates that are converted to the oxide by calcination at high temperatures. For example, heating yttrium hydroxy carbonate (basic yttrium carbonate) to a temperature greater than 600° C. results in the formation of $Y_2O_3$, which is useful in a number of electronic and ceramic applications. Yttrium hydroxy carbonate has also been prepared by the homogeneous precipitation method using urea and has been used for phosphate removal in aqueous systems (M. J. Haron et al., "Preparation of Basic Yttrium Carbonate for Phosphate Removal," *Water Environment Research*, 69, 1047-51, July/August 1997) and for arsenite and arsenate removal (Wasay, S. A. et al., "Removal of Arsenite and Arsenate Ions for Aqueous Solution by Basic Yttrium Carbonate," *Water Res. (G.B,)*, 30(5), 1143-1148 (1996).

The compositions of Formula (II) and Formula (III) comprise radioactive Y-90, Sm-153, Lu-177, or Ho-166 as their hydroxy carbonate compounds, or mixtures thereof, wherein their respective non-radioactive yttrium, samarium, holmium, or lutetium hydroxy carbonate compound may also be present.

Radioactive particles may be prepared by the homogeneous precipitation procedure using the appropriate metal salt(s) and urea, wherein the morphology, particle size, and size distribution are controlled by the reaction conditions employed in order to optimize in vivo performance. The use of the respective non-radioactive Y, Sm, Lu or Ho with their respective radioactive metal during the homogeneous precipitation procedure is especially preferred.

Combinations of these preferred radioactive metals can be used to prepare compositions that are useful for delivering a radiation dose to diseased cells. For example, both Y-90 and Sm-153 can be used in the homogeneous precipitation process. The particles are used to deliver the radiation dose to the synovial cavity or undesirable tissue mass (e.g. cancer).

An embodiment of the invention is to alter the Radioactive Hydroxy Carbonate particles by applying a Coat of a substance of a different composition. In this manner, the important properties of the radioactive particles are maintained while other properties such as decreased susceptibility to leaching, biocompatibility and physical and chemical integrity for in vivo applications can be optimized based on the nature of the surface Coat. A representation of a Coated Radioactive Hydroxy Carbonate particle of the invention is provided by Formula (II) wherein R is present (r is 1); Q, J, AN are not present (q, v and z all equal 0) and R, M*, w, x, y and n are defined as for Formula (I).

Another embodiment of the invention is to deposit onto existing Substrates that possess desirable properties [i.e. Q in Formula (I)] the Radioactive Hydroxy Carbonate compositions disclosed herein.

Non-radioactive hydroxy carbonates, such as yttrium hydroxy carbonate, have been deposited on a number of such substrates and have been reported in the literature. For example, particulate substrates include alumina powder (Kazuhiro Wataya, U.S. Pat. No. 6,080,485); silica particles [Herbert Giesche and Egon Matijevic, "Preparation, Characterization and Sinterability of Well-defined Silica/Yttria powders," *J. Mater. Res.*, 9(2), 436 (1994)]; barium titanate particles (Kazuhiro Wataya, U.S. Pat. No. 6,447,910); iron oxide particles [Bar Aiken and Egon Matijevic, "Preparation and Properties of Uniform Coated Inorganic Colloidal Particles IV. Yttrium Basic Carbonate and Yttrium Oxide on Hematite," *Journal of Colloid and Interface Science*, 126(2), 645-649 (1988)]; and polystyrene particles [Kawahashi, N., Matijevic, E., "Preparation and Properties of Uniform Colloid Particles V. Yttrium Basic Carbonate on Polystyrene Latex," *J. Colloid Interface Sci.*, 138(2), 534-542 (1990)]. The procedures and the teachings in these references for coating various surfaces with non-radioactive Rare-earth type metal hydroxy carbonate compounds are hereby incorporated by reference in their entirety.

Another embodiment of the invention is the use of the homogeneous precipitation process utilizing urea to deposit the Radioactive Hydroxy Carbonate on a Substrate to produce compositions represented by Formula (II). Compositions comprising the radioactive species are valuable for delivering the radiation dose to the synovial cavity or undesirable tissue mass. By choosing the initial Substrate, one can optimize the performance by selecting particular parameters such as the morphology, biodegradability, particle size and size distribution of the final composition. One such composition can be represented by Formula (II) wherein Q is present (i.e. q is 1); J, R and AN are not present (v, r and z are all 0) and Q, M*, w, x, y and n are defined as for Formula (I).

Suitable particles that can serve as Q are available from several commercial sources. Examples include polystyrene-polymethacrylate copolymers, silica, and poly(lactic acid) particles from nanometer to micron sizes which are available from micromod Partikeltechnologie GmbH, Friedrich-Barnewitz-St.4, 18119 Rostock-Warnemuende Germany (www.micromod.de). Also available from micromod are derivatives of the particles containing surface modifications such as —COOH, alkyl-OH, acrylate, $SiO_2$, and polyethyleneglycol (PEG). For example, a polystyrene-polymethacrylate polymer of a specific particle size that has been surface modified can be used as the Substrate Q.

Subsequently a Coat can be applied as represented by Formula (II) wherein Q and R are both present (i.e. q and r are both 1); and v and z both equal 0; and Q, R, M*, w, x, y and n are defined as for Formula (I).

Another embodiment of this invention is represented by Formula (III) wherein the co-precipitated aggregate contains iron and/or gadolinium oxides and/or hydroxides and wherein M*, w, x, y and n are as defined in Formula (I).

The preparation of non-radioactive hydrous stannic oxide, stannic hydroxide, and stannic oxyhydroxide and mixtures thereof has been reported in the literature. For example, Frank Austin Gooch and Claude Frederic Walker in their book *Outlines of Inorganic Chemistry* (which is hereby incorporated by reference for these teachings) have indicated that α-stannic hydroxides or α-stannic acids can be prepared by the addition of certain reagents to stannic salts. Thus, when sodium hydroxide is added in the proper quantity to a solution of stannic chloride, a white precipitate is formed which can contain the normal α-stannic hydroxide, $Sn(OH)_4$, but which yields upon analysis α-stannic oxyhydroxide, $SnO(OH)_2$, which is also known as α-stannic acid ($H_2SnO_3$). The α-stannic acid can also be prepared as a precipitate by adding sodium carbonate in the proper amount to a solution of stannic chloride and wherein carbon dioxide is evolved. Also, calcium carbonate, barium carbonate, and sodium sulfate can be added to stannic chloride to give a precipitate which when dried in air has the composition of α-stannic oxyhydroxide. Gooch and Walker also indicate that α-stannic acid can convert to β-stannic acid.

The homogeneous precipitation method using urea and a stannic salt can be advantageously used to produce the hydrous stannic oxide, stannic hydroxide, and stannic oxyhydroxide compounds discussed above. For example, Ki Chang Song and Yong Kang, *Materials Letters* 42, 283-289 (2000) prepared uniform non-radioactive particles in a narrow particle size range by heating urea and $SnCl_4$ in an aqueous solution at 90° C. for 4 hours. As the solution is heated, the urea is hydrolyzed and produces ammonia and carbon dioxide. The gradual and uniform rise in the pH of the solution results in the nucleation and growth of the uniform particles. By contrast, preparation of the Sn(IV) products by the addition of aqueous ammonia to a solution of the $SnCl_4$ resulted in a process that gave very little control of the particle size and shape.

Non-radioactive hydrous stannic oxide has been coated on $TiO_2$ by utilizing a homogeneous precipitation process using urea [Byung-Kwan Kim and Itaru Yasui, *Journal of Materials Science* 23, 637-642 (1988)].

The procedures and the teachings in the references cited above for preparing non-radioactive hydrous stannic oxide, stannic hydroxide, and stannic oxyhydroxide and for coating a particle with non-radioactive hydrous stannic oxide are hereby incorporated by reference in their entirety and are useful for the preparation of the compositions of Formula (IV) and Formula (V).

The compositions of Formula (IV) and Formula (V) comprising Sn(IV)-117m radioactive particles may be prepared by the above homogeneous precipitation procedure. The appropriate metal salt(s) and urea, in solvents such as water or alcohol/water mixtures, are heated by techniques generally known in the literature (including microwave heating). The morphology, particle size, and size distribution are controlled by the reaction conditions employed, including initial pH of the reactants, in order to optimize the product yield and in vivo performance. The particles are used to deliver the radiation dose to arthritic sites.

The compositions of Formula (III) and Formula (V) may be prepared by the homogeneous precipitation process wherein the appropriate metal salt(s) and urea in a solvent such as water are heated by techniques generally known in the literature. The compositions produced are effective in delivering a therapeutic radiation dose to the diseased cells such as the synovium or an undesirable tissue mass. In addition the paramagnetic properties of these compositions containing iron or gadolinium are useful for diagnostic purposes.

Another embodiment of this invention is to alter the Radioactive Sn Entity particles by applying a Coat of a substance of a different composition. In this manner, the important properties of the radioactive particles are maintained while other properties such as decreased susceptibility to leaching, biocompatibility and physical and chemical integrity for in vivo applications can be optimized based on the nature of the surface Coat. A representation of a Coated particle of the invention is provided by Formula (IV) wherein R is present (r is equal to 1); Q is not present (q is equal to 0). In general these compositions of Formula (IV) are those wherein r is equal to 1; q is equal to 0; and R, L, M, u, w, x, y, p and n are defined as for Formula (IV). Thus the Radioactive Sn Entity is present, a Coat is present, and the Hydroxy Carbonate Entity is optionally present (p is equal to 1 or 0).

Another embodiment of the invention is to deposit onto existing Substrates that possess desirable properties [i.e. Q in Formula (IV)] the Radioactive Sn Entity disclosed herein (q is equal to 1, p is equal to 1 or 0, r is equal to 0).

Another embodiment of the invention is the use of the homogeneous precipitation process utilizing urea to deposit the Radioactive Sn Entity on a Substrate to produce compositions represented by Formula (IV). Formulations comprising the radioactive species are valuable for delivering the radiation dose to arthritic sites. By choosing the initial Substrate, one can optimize the performance by selecting particular parameters such as the biodegradability, morphology, particle size and size distribution of the final composition. The compositions can be represented by Formula (IV) wherein Q is present (q is equal to 1); R is not present (r is equal to 0) and p is equal to 1 or 0, and Q, L, M, u, w, x, y and n are defined as in Formula (I).

Another embodiment of this invention is represented by Formula (IV) wherein Q is not present (q is equal to 0); R is not present (r is equal to 0); and p is equal to 1 or 0; and Sn, L and u are as defined in Formula (I). Formulations comprising this Radioactive Sn Entity are useful for delivering radiation doses to arthritic sites.

An additional aspect of the invention provides co-precipitated aggregate compositions as represented in Formula (V). One representation is wherein T is iron and/or gadolinium oxide and/or hydroxide; p is equal to 1 or 0; and Sn, L, M, u, w, w, y and n are as defined in Formula (I). Formulations comprising this Radioactive Sn Entity are useful for delivering radiation doses to arthritic sites.

Formulations

Certain compositions comprising the radioactive species of Formula (II) or Formula (IV) where Q is present are valuable for delivering the radiation dose to the synovial cavity [Formula (II) or Formula (IV)] or undesirable tissue mass [Formula (II)] because when certain properties are required (e.g. biodegradability, magnetic, or of a particular size), it is advantageous to have a selected Substrate that possesses the desirable properties.

An additional embodiment of the invention includes the use of iron oxide particles that are magnetic as the Substrate (Q). Preferred magnetic iron oxide particles include magnetite ($Fe_3O_4$), or its oxidized form maghemite (gamma $Fe_2O_3$), and hematite (alpha $Fe_2O_3$) with maghemite and magnetite often times being the most preferred. When iron oxide particles are used for in vivo applications it is important to add a protective layer or Coat to provide a low toxicity profile. Depositing the Radioactive Hydroxy Carbonate onto the iron oxide particles not only provides an effective treatment for arthritis or the undesirable tissue (e.g. cancer) but also acts as a protective barrier from the toxic nature of the naked magnetic iron oxide particles. Deposition of the Radioactive Hydroxy Carbonate can be achieved using the homogeneous precipitation process. One such composition can be represented by Formula (II) wherein Q is a magnetic iron oxide particle and q is equal to 1; J, R and AN are not present (v, r and z are all equal to 0). Another such composition can be represented by Formula (IV) wherein Q is a magnetic iron oxide particle and q is equal to 1; p is equal to 1 or 0; R is not present (r is 0).

The magnetic properties of the radioactive particles may be used to improve the localization of the composition by immobilizing the particles at the site of the synovium or targeted undesirable tissue mass, such as cancer, by controlling an applied external magnetic field. The particle size and a high degree of magnetization are optimized for peak performance. An additional benefit to the use of the magnetic iron oxide particles is that the active magnetic particles can be easily separated and purified from the reaction mixtures that were used for the initial preparations. If desirable, an additional component, such as silica, can be incorporated in the magnetic particle and can be represented by Formula (II) as Q, and the Radioactive Hydroxycarbonate is deposited thereon where J, AN and R are not present (v, z and r are all 0) or by Formula (IV) as Q, and the Radioactive Sn Entity is deposited thereon where p is 1 or 0 and R is not present (r is 0).

Compositions comprising the magnetic iron oxide derived radioactive species are valuable for delivering the radiation dose to the synovium or undesirable tissue mass.

Magnetic iron oxide particles useful for modification with radioactive metal hydroxy carbonates can be prepared by methods described in the literature. Non-limiting examples include:

(1) R. C. Plaza et al., *J. of Colloid and Interface Sci.*, 194, 398-407 (1977);

(2) Bar Aiken and Egon Matijevic; *Journal of Colloid and Interface Science*, 126(2) (1988);

(3) Zhi Ya Ma et al., *J. Mat. Chem.*, 19, 4695-4700 (2009);

(4) Pedro Tartaj, *J. Phys. D: Applied Phys.*, 36, R182-R197 (2003)

In addition, many commercial sources of suitable magnetic iron oxide particles are available and can be used as the Substrate (Q) in the present invention. Non-limiting examples include:

(1) Magnetic particles available from micromod Partikeltechnologie GmbH, Friedrich-Barnewitz-St.4, 18119 Rostock-Warnemuende Germany (www.micromod.de). Iron oxide particles without a surface modification are available as well as iron oxide particles that have been modified with additional surface chemistries. Examples include magnetic silica particles that are prepared by the hydrolysis of orthosilicates in the presence of magnetite that possess terminal Si—OH-bonds; "cluster-typed" magnetic silica particles; magnetic fluorescent silica particles; and silica-fortified magnetic dextran particles.

(2) Magnetic particles available from chemicell GmbH; Eresburgstrasse 22-23; 12103 Berlin; Germany (www-.chemicell.com). Examples include SiMAG particles that are magnetic silica beads that have either a highly porous or a non-porous silica surface; fluidMAG-UC/C and fluidMAG-UC/A which are magnetic nanoparticles with a cationic and anionic charge, respectively. Also available are hydroxyapatite coated magnetic particles with a diameter of approximately 2 microns.

(3) Nanosized magnetite particles coated with silica useful for hyperthermia applications available from Nanogap Subnmparticles; P.O. Box 591028; San Francisco, Calif.; 94159-0128 (http://nanogap.es/usa).

(4) Magnetic iron oxide ($Fe_3O_4$) nanocrystals and the nanocrystals coated with functional chemistries including silica, polyethyleneimine, polyethyleneglycol, polydiallyldimethylammonium chloride, oleic acid, dextran, carboxylic acid, and carboxylic acid plus polyethyleneglycol are available from M K Impex Corp.; Division: MKnano; 6382 Lisgar Drive; Missisauga, ON L5N 6X1; Canada.

An embodiment of the invention is the incorporation of an additional lanthanide metal ion into the Radioactive Hydroxy Carbonate entity. One such composition can be represented by Formula (II) wherein J is an additional lanthanide metal ion (i.e. v is greater than 0); Q, R and AN are not present (i.e. q, r and z are all equal to 0) and J, M*, w, x, y and n are defined as for Formula (I).

Lanthanide based particles represent a class of compounds that possess fluorescence properties with high emission properties and as such have been used as luminescent markers in biological systems. A fluorescent lanthanide metal can be incorporated in the Radioactive Hydroxy Carbonate particles utilizing the homogeneous precipitation process employing urea and the radioactive metal salt plus the lanthanide metal salt. Certain compounds can be represented by Formula (II), wherein J is a fluorescent lanthanide such as gadolinium, europium or erbium. The compounds can also have an additional Coating, R, if desired (i.e. r is equal to 1); and Q and AN are not present (i.e. q and z are equal to 0).

The Radioactive Hydroxy Carbonate entity containing the additional lanthanide metal ion, J (i.e. v is greater than 0), wherein for example J represents a fluorescent lanthanide can be deposited onto Substrate Q (e.g. magnetic particles). The compounds can be represented by Formula (II) where q is equal to 1 and Q is a magnetic iron oxide particle; and R and AN are not present (i.e. r and z are both equal to 0).

If desired, an additional Coat R (i.e. r is equal to 1) can be incorporated and the magnetic iron particles can have a surface modification. The compositions can act as biological luminescent markers that can be advantageously controlled by a magnetic field to deliver a therapeutic radiation dose to the synovium or an undesirable tissue mass.

An embodiment of the invention is the incorporation of an additional pharmaceutically-acceptable anionic moiety AN into the Radioactive Hydroxy Carbonate entity without Substrate Q and Coat R present. These compositions are represented by Formula (II) wherein z is greater than 0; and q and r are both equal to 0 and AN, M*, w, x, y and n are defined as for Formula (I).

AN is a pharmaceutically-acceptable anionic moiety, examples include but are not limited to nitrate, chloride, hydrogen phosphate, dihydrogen phosphate, fluoride, sulfate and oxalate. If desired, the compounds can have a Coat R and/or Substrate Q present as described earlier.

Another embodiment of the invention is to modify the surface of the Radioactive Hydroxy Carbonate entity of Formula (II) where r is equal to 0 or the Radioactive Sn Entity of Formula (IV) where r is equal to 0 with functional groups known in the literature [e.g. $NH_2$ groups generated by functionalization using (3-aminopropyl)trimethoxysilane] that can then be used for attachment to tumor-targeting species such as monoclonal antibodies, proteins, or small molecules. The compounds are useful for delivering therapeutically effective doses of radiation to cancerous sites.

Further embodiments of the invention are compositions that are useful for the treatment of the synovium or undesirable tissue masses comprising as a first component compositions of Formula (II), Formula (III), Formula (IV) and Formula (V) and certain derivatives and modifications thereof, as described herein, as a therapeutically effective component of a treatment modality comprising as a second component nano-sized iron oxide particles, preferably magnetic magnetite and maghemite [about 10 to about 50 nanometers (nm)], which have been Coated with a protective Coating. These compositions are injected directly into or near to the site of diseased cells (e.g. a diseased synovium) or the undesirable tissue mass (e.g. tumor), either simultaneously with, or shortly before, or shortly after the administration of the first component radioactive particles (where shortly means from about 1 sec. to about 30 min.). The magnetic properties of the iron oxide particles are utilized to generate a temperature (approximately from 42-46° C.) that weakens and/or kills the tumor when the particles are exposed to an external stimulus such as an alternating current (AC) magnetic field (hyperthermic conditions), while the radioactive metal that is present delivers a therapeutic dose to the tumor. Both components can be comprised of magnetic iron oxide particles. In some cases, nano-size iron oxide particles of about 10 nm to about 50 nm can be Q in Formula (II) or Formula (IV), if desired, an optional Coating R may be used, to achieve both goals (hyperthermia treatment and delivering a therapeutic radiation dose).

Formulations and Method of Use

Once formed, the radioactive particles of Formula (I) and certain derivatives and modifications thereof can be administered in a therapeutically-acceptable dose and in a pharmaceutically-acceptable liquid such as water or saline. The various compositions of Formula (II) and Formula (III) are useful for treating an animal or human having diseased cells that need ablation (e.g. an undesirable tissue mass or the synovium) by administering a therapeutically effective dose of a suitable pharmaceutically-acceptable composition by injection into or near such diseased cells. Such diseased cells may be caused by a variety of diseases (e.g. cancers), arthritis or infections (e.g. osteomyelitis). The various compositions of Formula (IV) and Formula (V) are useful for treating an animal or human having arthritic sites by administering a therapeutically effective dose of a suitable pharmaceutically-acceptable composition by injection into or near the synovial cavity.

The formulated compositions may be, but are not limited to, suspensions, slurries, or colloids. Optionally, other known, usual pharmaceutically-acceptable ingredients can be present in the composition such as excipients, suspension aids, preservatives, buffers for pH adjustment, crystal growth modifiers, and others, which are well known to one skilled in this art.

In another aspect of this invention, compositions containing insoluble particles are separated from the initial reaction mixture (e.g. by filtering, centrifuging, or decanting) and a therapeutically-effective dose of the insoluble particles is administered in a pharmaceutically-acceptable liquid into or near the diseased cells.

Delivery of the formulated composition can be done using a microsyringe or a pump capable of accurately delivering microliter volumes (e.g. Valco Instrument Company, Inc. model CP-DSM) to provide flow to the proximal end of a catheter which may be placed within or next to the undesirable tissue mass to be treated. The flow may be either continuous or may be pulsed to enhance complete penetration of the undesirable tissue mass by the radioisotope.

Therapeutically-effective doses of radioisotopes will require different amounts of activity for different isotopes and for different indications but can be described by the radiation dose delivered to the tissue.

In one embodiment of the invention, the compositions of Formula (II) or Formula (III) may be delivered to a bone tumor using a miniature pump or syringe. Access to the tumor may be effected by the use of a bone biopsy tool or a miniature drill capable of making a curved or angled hole through bone and either upstream of the tumor (so to guide the catheter towards it) or directly into the bone or tumor in the bone. Any device that can provide a suitable hole in the bone, such as a syringe needle or biopsy tool will suffice. The insertion of the catheter using imaging techniques, as is known in the art, may help to position the distal end of the catheter in close proximity to the tumor. Some known imaging techniques for this use are PET, CT, Ultrasound, MRI, and fluoroscopy; particularly useful are PET or CT.

The compositions disclosed herein may be used in conjunction with techniques known in the art for the therapeutic treatment of diseased cells such as arthritis or undesirable tissue masses (e.g. cancer or infections). The present compositions of Formula (I) may also be part of a combination therapy with other known therapeutic drugs or treatments.

This invention will be further clarified by a consideration of the following examples, which are intended to be purely exemplary of the present invention. The numbered examples are illustrative of this invention; the lettered examples are comparative examples.

EXAMPLES

Example 1

Preparation of Composition (Y-90, 2.4 M Urea, 0.1 M YCl$_3$ Heated 45 min)

Y-90 was received from Perkin Elmer as yttrium chloride in a minimal volume of 0.05M HCl. Activity was measured to be 440 mCi using a Capintec CRC-55 dose calibrator. The activity concentration was adjusted to 20 µCi/µL by the addition of 19 µL of 0.05 M HCl.

95 µL of 5 M urea was mixed with 95 µL of 0.2 M YCl$_3$ and 10 µL of Y-90 (prepared above) in a small screw cap conical micro-centrifuge tube. The solution and mixed for 5 sec using a VWR mini vortexer. The vial was then clamped onto a ring stand and lowered into a 100 mL beaker of boiling water for 45 min.

The composition of this example is representative of both Formula (I) wherein q, t, b, c, r and v are all equal to 0, a is equal to 1, and M* is Y-90; and Formula (II) wherein q, v and r are all equal to 0, and M* is Y-90.

Example 2

Composition of Example 1 Administered to Mouse Muscle and Rat Knee

Six male BALB/c mice, under Isoflurane anesthesia, were each injected with 20 µL of the Composition prepared according to the procedure of Example 1 into the gastrocnemius muscle of the right hind leg using a ⅓ cc insulin syringe. The mice were individually housed in cages with absorbent paper under a wire mesh bottom.

Mice were sacrificed at 6 days (about 2 half-lives), 8 days (about 3 half-lives) and 11 days (about 4 half-lives) in groups of two. Organs and tissues collected were: right leg (including injection site), blood, heart, lung, left femur, left thigh, liver, spleen, kidneys, small intestine, large intestine, stomach, remainder of carcass, and bladder along with all collected absorbent paper containing accumulated feces and urine. The carcass consists of the remaining musculoskeletal structure, reproductive organs, the skin, head, limbs and tail. The right leg that was collected was removed just below the hip joint and consists of the entire limb, including the injection site.

Samples were counted for radioactivity on a PerkinElmer Wizard automated NaI well detector. The data, shown below in Table 1, indicate the average percent injected dose (% ID) in each tissue/sample.

Six male Sprague Dawley rats, under Isoflurane anesthesia, were each injected with 20 µL of the Composition prepared according to the procedure of Example 1 into the synovial cavity of the right hind knee using a ⅓ cc insulin syringe. The dose was deposited into the cavity via needle insertion through the skin. The rats were individually housed in cages with absorbent paper under a wire mesh bottom.

Rats were sacrificed at 6 days (about 2 half-lives), 8 days (about 3 half-lives) and 11 days (about 4 half-lives) in groups of two. Organs and tissues collected were: right leg (including injection site), blood, heart, lung, left femur, left thigh, liver, spleen, kidneys, small intestine, large intestine, stomach, and bladder along with all collected absorbent paper containing accumulated feces and urine. The right leg that was collected was removed just below the hip joint and consists of the entire limb, including the injection site.

Due to the size of the animals, the carcass was not collected and measured as was done for the mice. The % ID in the skeletal structure, muscular structure and blood in the body were calculated from the activity in samples of those tissues (left femur, left thigh, blood) and rat body weight using equations fitted to data in the literature as was described earlier.

Samples were counted for radioactivity on a PerkinElmer Wizard automated NaI well detector. The data, shown below in Table 1, indicate the average percent injected dose in each tissue/sample.

TABLE 1

| | Average % Injected Dose (% ID) of Y-90 | | | | | |
| --- | --- | --- | --- | --- | --- | --- |
| | Mice | | | Rats | | |
| | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.0 | 0.0 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.1 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.3 | 0.1 | 0.1 | — | — | — |
| Leg (including injection site) | 99.4 | 99.8 | 99.7 | 99.3 | 99.7 | 100.0 |
| Urine/Feces | 0.2 | 0.1 | 0.2 | 0.6 | 0.3 | 0.0 |

Example 3

Preparation of Composition (Y-90, 2.4 M Urea, 0.02 M YCl₃ Heated 45 min)

95 µL of 5 M urea was mixed with 95 µL of 0.04 M YCl$_3$ and 10 µL of Y-90 (prepared according to the procedure of Example 1) in a small screw cap conical micro-centrifuge tube. The solution was mixed for 5 sec with a VWR mini vortexer. The vial was then clamped onto a ring stand and lowered into a 100 mL beaker of boiling water for 45 min The composition of this example is representative of both Formula (I) wherein q, t, b, c, r and v are all equal to 0, a is equal to 1, and M* is Y-90; and Formula (II) wherein q, v and r are all equal to 0, and M* is Y-90.

Example 4

Composition of Example 3 Administered to Mouse Muscle and Rat Knee

Six male BALB/c mice and six male Sprague Dawley rats were each injected, housed, sacrificed and assayed in the manner of Example 2 using 20 µL of the Composition prepared according to the procedure of Example 3. The data, shown below in Table 2, indicate the average percent injected dose (% ID) in each tissue/sample.

TABLE 2

| Average % Injected Dose (% ID) of Y-90 | | | | | | |
|---|---|---|---|---|---|---|
| | Mice | | | Rats | | |
| | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.0 | 0.0 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.0 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.1 | 0.1 | 0.2 | — | — | — |
| Leg (including injection site) | 99.9 | 99.9 | 99.8 | 99.6 | 99.8 | 99.8 |
| Urine/Feces | 0.1 | 0.0 | 0.1 | 0.3 | 0.2 | 0.1 |

Example 5

Preparation of Composition (Y-90, 0.24 M Urea, 0.01 M YCl₃ Heated 2 hr)

Y-90 was received from Perkin Elmer as yttrium chloride in a minimal volume of 0.05 M HCl. Activity was measured to be about 10 mCi using a Capintec CRC-55 dose calibrator. The activity concentration was adjusted to about 40 µCi/µL by the addition of 0.05 M HCl.

95 µL of 0.5 M urea was mixed with 95 µL of 0.02 M YCl$_3$ and 10 µL of the Y-90 (prepared above) in a small screw-cap conical micro-centrifuge tube. The solution was mixed for 5 sec using a VWR Mini Vortexer. The vial was then clamped onto a ring stand and lowered into a 100 mL beaker of boiling water for 2 hr.

The composition of this example is representative of both Formula (I) wherein q, t, b, c, r and v are all equal to 0, a is equal to 1, and M* is Y-90; and Formula (II) wherein q, v and r are all equal to 0, and M* is Y-90.

Example 6

Composition of Example 5 Administered to Mouse Muscle

Six male BALB/c mice were each injected, housed, sacrificed and assayed in the manner of Example 2 using 20 µL of the Composition prepared according to the procedure of Example 5. The data, shown below in Table 3, indicate the average percent injected dose (% ID) in each tissue/sample.

TABLE 3

| Average % Dose Injection (% ID) of Y-90 | | | |
|---|---|---|---|
| | 6 days | 8 days | 11 days |
| Blood | 0.0 | 0.0 | 0.0 |
| Heart | 0.0 | 0.0 | 0.0 |
| Lung | 0.0 | 0.0 | 0.0 |
| Left Femur | 0.0 | 0.0 | 0.0 |
| Left Thigh | 0.0 | 0.0 | 0.0 |
| Liver | 0.0 | 0.0 | 0.0 |
| Spleen | 0.0 | 0.0 | 0.0 |
| Kidney | 0.0 | 0.0 | 0.0 |
| Sm. Intestine | 0.0 | 0.0 | 0.0 |
| Lg. Intestine | 0.0 | 0.0 | 0.0 |
| Stomach | 0.0 | 0.0 | 0.0 |
| Carcass | 0.6 | 0.6 | 0.4 |
| Leg (including injection site) | 97.5 | 98.6 | 99.2 |
| Urine/Feces | 1.9 | 0.8 | 0.4 |

Example 7

Preparation of Composition (Y-90, 0.04 M FeCl₃, 0.01 M YCl₃ 2.4 M Urea Heated 4 hr)

Y-90 was received from Perkin Elmer as yttrium chloride in a minimal volume of 0.05M HCl. Activity was measured to be 13 mCi using a Capintec CRC-55 dose calibrator. The activity concentration was adjusted to 30.5 µCi/µL by adding 24.5 µL of 0.05 M HCl to 0.5 µL of Y-90.

125 µL of 0.16 M FeCl$_3$ was mixed with 125 µL of 0.04 M YCl$_3$ and 250 µL of 5 M urea in a small screw cap conical micro-centrifuge tube. 25 µL of Y-90 (prepared above) was added to the solution and mixed for 5 sec with a VWR mini vortexer. The vial was then clamped onto a ring stand and lowered into a 100 mL beaker of water at approximately 90° C. for 4 hr.

The composition of this example is representative of both Formula (I) wherein q, b, c, r and v are all equal to 0, t and a are both equal to 1, and M* is Y-90; and Formula (III) wherein M* is Y-90.

Example 8

Composition of Example 7 Administered to Mouse Muscle and Rat Knee

Six male BALB/c mice and six male Sprague Dawley rats were each injected, housed, sacrificed and assayed in the manner of Example 2 using 20 μL of the Composition prepared according to the procedure of Example 7. The data, shown below in Table 4, indicate the average percent injected dose (% ID) in each tissue/sample.

TABLE 4

Average % Injected Dose (% ID) of Y-90

|  | Mice | | | Rats | | |
| --- | --- | --- | --- | --- | --- | --- |
|  | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.6 | 0.5 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.1 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.2 | 0.4 | 0.3 | — | — | — |
| Leg (including injection site) | 99.7 | 99.5 | 99.7 | 98.9 | 98.9 | 99.6 |
| Urine/Feces | 0.1 | 0.1 | 0.0 | 0.5 | 0.6 | 0.3 |

Example 9

Preparation of Composition (Y-90, 2.2 M Urea, 0.1 M YCl$_3$—Urease Initiated)

Y-90 was received from Perkin Elmer in a minimal volume of 0.05M HCl. Activity was measured to be about 1.18 mCi using a Capintec CRC-55 dose calibrator. The activity was adjusted to about 40 μCi/μL by the addition of 44 μL of 0.05 M HCl.

152 μL 5 M urea was mixed with 152 μL of 0.2 M YCl$_3$ and 16 μL of the Y-90 solution (prepared above) in a screw cap micro-centrifuge tube. The solution was mixed for 5 sec using a VWR mini vortexer. The pH was determined to be around 5 using pH strips. With a micropipette, 20 μL of an acetate-buffered, 20 mg/mL urease solution was added to the vial and placed on a nutator and gently agitated for 1 hr at room temperature. 300 μL of the supernatant was carefully removed with a micropipette. The activity of the removed supernatant was 3.2 μCi. To the original vial, 300 μL of saline solution was added and the vial was mixed with a mini vortexer for about 1 min.

The composition of this example is representative of both Formula (I) wherein q, t, b, c, r and v are all equal to 0, a is equal to 1, and M* is Y-90; and Formula (II) wherein q, v and r are all equal to 0, and M* is Y-90.

Example 10

Composition of Example 9 Administered to Mouse Muscle and Rat Knee

Six male BALB/c mice and six male Sprague Dawley rats were each injected, housed, sacrificed and assayed in the manner of Example 2 using 20 μL of the Composition prepared according to the procedure of Example 9. The data, shown below in Table 5, indicate the average percent injected dose (% ID) in each tissue/sample.

TABLE 5

Average % Injected Dose (% ID) of Y-90

|  | Mice | | | Rats | | |
| --- | --- | --- | --- | --- | --- | --- |
|  | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.0 | 0.0 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.0 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.0 | 0.0 | 0.0 | — | — | — |
| Leg (including injection site) | 100.0 | 100.0 | 100.0 | 100.0 | 100.0 | 100.0 |
| Urine/Feces | 0.0 | 0.0 | 0.0 | 0.0 | 0.0 | 0.0 |

Example 11

Preparation of Composition (Sm-153, 2.3 M Urea, 0.1 M YCl$_3$ Heated 45 min)

Sm-153 was received from MURR as samarium chloride in 0.05M HCl. Activity was measured to be 2.2 mCi using a Capintec CRC-55 dose calibrator. To increase the dose concentration, the solution was placed in a heating block at about 90° C. to evaporate the excess. After 40 min, the solution was removed from heat and 70 μL was transferred to a small screw cap conical micro-centrifuge tube. The activity of the measured aliquot was 350 μCi. The final activity concentration was 5 μCi per μL.

152 μL of 5 M urea was mixed with 152 μL of 0.2 M YCl$_3$ and 32 μL of the Sm-153 (prepared above) in a small screw cap conical micro-centrifuge tube. The activity of the solution was 166.8 μCi. The entire solution was mixed for 5 sec using a VWR mini vortexer. The vial was then clamped onto a ring stand and lowered into a 100 mL beaker of boiling water for 45 min.

The composition of this example is representative of both Formula (I) wherein q, t, b, c, r and v are all equal to 0, a is equal to 1, and M* is Sm-153, also containing non-radioactive Y; and Formula (II) wherein q, v and r are all equal to 0, and M* is Sm-153, also containing non-radioactive Y.

Example 12

Composition of Example 11 Administered to Mouse Muscle and Rat Knee

Six male BALB/c mice and six male Sprague Dawley rats were each injected and housed in the manner of Example 2 using 20 μL of the Composition prepared according to the procedure of Example 11. The animals were sacrificed at 4 days (about 2.1 half-lives), 7 days (about 3.6 half-lives) and 8 days (about 4.1 half-lives) in groups of two and assayed in the manner of Example 2. The data, shown below in Table 6, indicate the average percent injected dose (% ID) in each tissue/sample.

TABLE 6

Average % Injected Dose (% ID) of Sm-153

| | Mice | | | Rats | | |
|---|---|---|---|---|---|---|
| | 4 days | 7 days | 8 days | 4 days | 7 days | 8 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.0 | 0.0 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.0 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.1 | 0.0 | 0.0 | — | — | — |
| Leg (including injection site) | 99.9 | 99.8 | 100.0 | 99.9 | 100.0 | 99.9 |
| Urine/Feces | 0.0 | 0.2 | 0.0 | 0.1 | 0.0 | 0.1 |

Example 13

Preparation of Composition (Ho-166, 2.4 M Urea, 0.08 M HoCl$_3$ Heated 45 min)

Ho-166 was received from MURR as holmium chloride in 850 µL of 0.05M HCl. The activity was measured to be 1 mCi using a Capintec CRC-55 dose calibrator. To increase the dose concentration, the solution was placed in a heating block at about 90° C. to evaporate the excess liquid. After 40 min, the solution was removed from heat and 50 µL was taken and placed in a small screw cap conical micro-centrifuge tube. The activity of the measured aliquot was 800 µCi. The final activity concentration was 16 µCi per µL.

114 µL of 5 M urea was mixed with 114 µL of 0.17 M HoCl$_3$ and 12 µL of Ho-166 (prepared above) in a small screw cap conical micro-centrifuge tube. The solution was mixed for 5 sec using a VWR mini vortexer. The vial was then clamped onto a ring stand and lowered into a 100 mL beaker of boiling water for 45 min.

The composition of this example is representative of both Formula (I) wherein q, t, b, c, r and v are all equal to 0, a is equal to 1, and M* is Ho-166; and Formula (II) wherein q, v and r are all equal to 0, and M* is Ho-166.

Example 14

Composition of Example 13 Administered to Mouse Muscle

Six male BALB/c mice were each injected and housed in the manner of Example 2 using 20 µL of the Composition prepared according to the procedure of Example 13. The animals were sacrificed at 2 days (about 2 half-lives), 3 days (about 3 half-lives) and 4 days (about 4 half-lives) in groups of two and assayed in the manner of Example 2. The data, shown below in Table 7, indicate the average percent injected dose (% ID) in each tissue/sample.

TABLE 7

Average % Injected Dose (% ID) of Ho-166

| | 2 days | 3 days | 4 days |
|---|---|---|---|
| Blood | 0.0 | 0.0 | 0.0 |
| Heart | 0.0 | 0.0 | 0.0 |
| Lung | 0.0 | 0.0 | 0.0 |
| Left Femur | 0.0 | 0.0 | 0.0 |
| Left Thigh | 0.0 | 0.0 | 0.0 |
| Liver | 0.0 | 0.0 | 0.0 |
| Spleen | 0.0 | 0.0 | 0.0 |
| Kidney | 0.0 | 0.0 | 0.0 |
| Small Intestine | 0.0 | 0.0 | 0.0 |
| Large Intestine | 0.0 | 0.0 | 0.0 |
| Stomach | 0.0 | 0.0 | 0.0 |
| Carcass | 0.0 | 0.0 | 0.0 |
| Leg (including injection site) | 99.9 | 99.9 | 99.9 |
| Urine/Feces | 0.1 | 0.1 | 0.1 |

Example 15

Preparation of Composition (Ho-166, 2.4 M Urea, 0.02 M HoCl$_3$ Heated 45 min)

114 µL of 5 M Urea was mixed with 114 µL of 0.04 M HoCl$_3$ and 12 µL of Ho-166 (prepared according to the procedure of Example 13) in a small screw cap conical micro-centrifuge tube. The solution was mixed for 5 sec using a VWR mini vortexer. The vial was then clamped onto a ring stand and lowered into a 100 mL beaker of boiling water for 45 min.

The composition of this example is representative of both Formula (I) wherein q, t, b, c, r and v are all equal to 0, a is equal to 1, and M* is Ho-166; and Formula (II) wherein q, v and r are all equal to 0, and M* is Ho-166.

Example 16

Composition of Example 15 Administered to Rat Knee

Six male Sprague Dawley rats were each injected and housed in the manner of Example 2 using 20 µL of the Composition prepared according to the procedure of Example 15. The animals were sacrificed at 2 days (about 2 half-lives), 3 days (about 3 half-lives) and 4 days (about 4 half-lives) in groups of two and assayed in the manner of Example 2. The data, shown below in Table 8, indicate the average percent injected dose (% ID) in each tissue/sample.

TABLE 8

Average % Injected Dose (% ID) of Ho-166

| | 2 days | 3 days | 4 days |
|---|---|---|---|
| Calculated Blood | 0.0 | 0.0 | 0.0 |
| Heart | 0.0 | 0.0 | 0.0 |
| Lung | 0.0 | 0.0 | 0.0 |
| Calculated Skeleton | 0.0 | 0.0 | 0.0 |
| Calculated Muscle | 0.0 | 0.0 | 0.0 |
| Liver | 0.0 | 0.1 | 0.0 |
| Spleen | 0.0 | 0.0 | 0.0 |
| Kidney | 0.0 | 0.0 | 0.0 |

TABLE 8-continued

Average % Injected Dose (% ID) of Ho-166

|  | 2 days | 3 days | 4 days |
|---|---|---|---|
| Sm. Intestine | 0.0 | 0.0 | 0.0 |
| Lg. Intestine | 0.0 | 0.0 | 0.0 |
| Stomach | 0.0 | 0.0 | 0.0 |
| Leg (injection site) | 100.0 | 99.8 | 100.0 |
| Urine/Feces | 0.0 | 0.1 | 0.0 |

Example 17

Preparation of Composition (Lu-177, 2.4 M Urea, 0.1 M LuCl₃ Heated 45 min)

Lu-177 was received from Perkin Elmer as lutetium chloride in a minimal volume of 0.05 M HCl. 95 μL of 5 M urea was mixed with 95 μL of 0.2 M LuCl₃ and 10 μL of Lu-177 in a small screw cap conical micro-centrifuge tube. The solution was mixed for 5 sec using a VWR mini vortexer. The vial was then clamped onto a ring stand and lowered into a 100 mL beaker of water at about 90° C. for 45 min.

The composition of this example is representative of both Formula (I) wherein q, t, b, c, r and v are all equal to 0, a is equal to 1, and M* is Lu-177; and Formula (II) wherein q, v and r are all equal to 0, and M* is Lu-177.

Example 18

Composition of Example 17 Administered to Mouse Muscle and Rat Knee

Six male BALB/c mice and six male Sprague Dawley rats were each injected and housed in the manner of Example 2 using 20 μL of the Composition prepared according to the procedure of Example 17. The animals were sacrificed at 12 days (about 2 half-lives), 19 days (about 3 half-lives) and 25 days (about 4 half-lives) in groups of two and assayed in the manner of Example 2. The data, shown below in Table 9, indicate the average percent injected dose (% ID) in each tissue/sample.

TABLE 9

Average % Injected Dose (% ID) of Lu-177

|  | Mice | | | Rats | | |
|---|---|---|---|---|---|---|
|  | 12 days | 19 days | 25 days | 12 days | 19 days | 25 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.7 | 1.0 | 1.1 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.1 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |

TABLE 9-continued

Average % Injected Dose (% ID) of Lu-177

|  | Mice | | | Rats | | |
|---|---|---|---|---|---|---|
|  | 12 days | 19 days | 25 days | 12 days | 19 days | 25 days |
| Carcass | 0.2 | 0.2 | 0.2 | — | — | — |
| Leg (including injection site) | 99.7 | 99.7 | 99.7 | 98.8 | 98.7 | 98.6 |
| Urine/Feces | 0.1 | 0.0 | 0.1 | 0.3 | 0.3 | 0.3 |

Example 19

Preparation of Composition (Y-90 Coated 2.0 μm Magnetic Hydroxyapatite Particles—Heat Initiated)

Y-90 was received from Perkin Elmer in a minimal volume of 0.05M HCl. Activity was measured to be about 1.187 mCi using a Capintec CRC-55 dose calibrator. The activity concentration was adjusted to about 31.24 μCi/μL by the addition of 0.05 M HCl.

2.1 μL of a 50 mg/mL slurry of 2.0 μm magnetic hydroxyapatite particles (chemicell GmbH) in distilled water was mixed with 209 μL of 8.6 M urea, 10 μL of 0.3 M YCl₃ and 777 μL of distilled water in a screw cap micro-centrifuge tube and then mixed for 5 sec using a VWR mini vortexer. With a micropipette, 375 μL was removed and placed in a separate micro-centrifuge tube. 15 μL of the Y-90 solution (prepared above) was added to the new vial. The activity was measured to be 381 μCi. The vial was then clamped onto a ring stand and lowered into a 100 mL beaker of water at about 90° C. for 4 hr. The mixture was shaken by hand every 30 min to re-suspend the particles.

After heating, the vial was placed next to a magnet for 2 min. The magnetic particles were attracted to one side of the vial, allowing 325 μL of the supernatant to be easily removed. The activity of the supernatant was 19.02 μCi. To bring the particles back into suspension, 325 μL of saline was added and then the mixture was vortexed for 5 sec.

The composition of this example is representative of both Formula (I) wherein t, b, c, r and v are all equal to 0, q and a are both equal to 1, and M* is Y-90; and Formula (II) wherein v and r are both equal to 0, q is equal to 1, and M* is Y-90.

Example 20

Composition of Example 19 Administered to Mouse Muscle

Six male BALB/c mice were each injected, housed, sacrificed and assayed in the manner of Example 2 using 20 μL of the Composition prepared according to the procedure of Example 19. The data, shown below in Table 10, indicate the average percent injected dose (% ID) in each tissue/sample.

TABLE 10

Average % Dose Injection (% ID) of Y-90

|  | 6 days | 8 days | 11 days |
|---|---|---|---|
| Blood | 0.0 | 0.0 | 0.0 |
| Heart | 0.0 | 0.0 | 0.0 |

TABLE 10-continued

Average % Dose Injection (% ID) of Y-90

|  | 6 days | 8 days | 11 days |
|---|---|---|---|
| Lung | 0.0 | 0.0 | 0.0 |
| Left Femur | 0.0 | 0.0 | 0.0 |
| Left Thigh | 0.0 | 0.0 | 0.0 |
| Liver | 0.0 | 0.0 | 0.0 |
| Spleen | 0.0 | 0.0 | 0.0 |
| Kidney | 0.0 | 0.0 | 0.0 |
| Small Intestine | 0.0 | 0.0 | 0.0 |
| Large Intestine | 0.0 | 0.0 | 0.0 |
| Stomach | 0.0 | 0.0 | 0.0 |
| Carcass | 0.3 | 0.4 | 0.6 |
| Leg (including injection site) | 99.5 | 99.5 | 99.3 |
| Urine/Feces | 0.2 | 0.1 | 0.1 |

Example 21

Preparation of Composition (Y-90 Coated 2.0 μm Magnetic Hydroxyapatite Particles—Urease initiated)

Y-90 was received from Perkin Elmer in a minimal volume of 0.05M HCl. Activity was measured to be about 1.18 mCi using a Capintec CRC-55 dose calibrator. The activity concentration was adjusted to about 40 μCi/μL by the addition of 44 μL of 0.05 M HCl.

2.1 μL of a 50 mg/mL slurry of 2.0 μm magnetic hydroxyapatite particles in distilled water was mixed with 209 μL of 8.6 M Urea, 10 μL of 0.3 M YCl$_3$ and 777 μL of distilled water in a screw cap micro-centrifuge tube and then mixed for 5 sec using a VWR mini vortexer. With a micropipette, 375 μL was removed and placed in a separate micro-centrifuge tube. 15 μL of the Y-90 solution (prepared above) was added to the new vial and mixed for 5 sec with the mini vortexer. Then 25 μL of an acetate-buffered, 20 mg/mL urease solution was added and the vial was vortexed for 5 sec. The mixture was placed in a nutator for 1 hr with gentle agitation.

Afterwards, the vial was placed on a magnetic stand for 2 min. The magnetic particles were collected on one side of the vial, allowing 360 μL of the supernatant to be easily removed. To bring the particles back into suspension, 360 μL of saline was added and the mixture was vortexed for 5 sec.

The composition of this example is representative of both Formula (I) wherein t, b, c, r and v are all equal to 0, q and a are both equal to 1, and M* is Y-90; and Formula (II) wherein v and r are both equal to 0, q is equal to 1, and M* is Y-90.

Example 22

Composition of Example 21 Administered to Mouse Muscle and Rat Knee

Six male BALB/c mice and six male Sprague Dawley rats were each injected, housed, sacrificed and assayed in the manner of Example 2 using 20 μL of the Composition prepared according to the procedure of Example 21. The data, shown below in Table 11, indicate the average percent injected dose (% ID) in each tissue/sample.

TABLE 11

Average % Injected Dose (% ID) of Y-90

|  | Mice | | | Rats | | |
|---|---|---|---|---|---|---|
|  | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.5 | 0.0 | 0.0 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.1 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.1 | 0.6 | 0.0 | — | — | — |
| Leg (including injection site) | 99.8 | 99.2 | 100.0 | 98.3 | 98.2 | 99.1 |
| Urine/Feces | 0.1 | 0.2 | 0.0 | 1.1 | 1.8 | 0.9 |

Example 23

Preparation of Composition (Y-90 Coated 5.0 μm Hydroxyapatite Particles—Heat Initiated)

Y-90 was received from Perkin Elmer in a minimal volume of 0.05M HCl. Activity was measured to be about 1.187 mCi using a Capintec CRC-55 dose calibrator. The activity concentration was adjusted to about 31.24 μCi/μL by the addition of 0.05 M HCl.

2.1 μL of a 50 mg/mL slurry of 5.0 μm hydroxyapatite particles (Fluidnova) in distilled water was mixed with 209 μL of 8.6 M urea, 10 μL of 0.3 M YCl$_3$ and 777 μL of distilled water in a screw cap micro-centrifuge tube and mixed for 5 sec using a VWR mini vortexer. With a micropipette, 300 μL was removed and placed in a separate micro-centrifuge tube. 12 μL of the Y-90 solution (prepared above) was added to the new vial. The activity was measured to be 380 μCi. A small disc-shaped magnetic stir bar was placed into the vial and the vial was clamped onto a ring stand and lowered into a 100 mL beaker of water and stirred and heated at about 90° C. for 4 hr.

The composition of this example is representative of both Formula (I) wherein t, b, c, r and v are all equal to 0, q and a are both equal to 1, and M* is Y-90; and Formula (II) wherein v and r are both equal to 0, q is equal to 1, and M* is Y-90.

Example 24

Composition of Example 23 Administered to Mouse Muscle and Rat Knee

Six male BALB/c mice and six male Sprague Dawley rats were each injected, housed, sacrificed and assayed in the manner of Example 2 using 20 μL of the Composition prepared according to the procedure of Example 23. The data, shown below in Table 12, indicate the average percent injected dose (% ID) in each tissue/sample.

TABLE 12

Average % Injected Dose (% ID)

| | Mice | | | Rats | | |
|---|---|---|---|---|---|---|
| | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.0 | 0.0 | 0.0 | 0.0 | 0.0 | 0.0 |
| Lung | 0.0 | 0.0 | 0.0 | 0.0 | 0.0 | 0.0 |
| Left Femur | 0.0 | 0.0 | 0.0 | — | — | — |
| Calculated Skeleton | — | — | — | 0.9 | 0.8 | 0.2 |
| Left Thigh | 0.0 | 0.0 | 0.0 | — | — | — |
| Calculated Muscle | — | — | — | 0.0 | 0.0 | 0.0 |
| Liver | 0.0 | 0.0 | 0.0 | 0.1 | 0.0 | 0.0 |
| Spleen | 0.0 | 0.0 | 0.0 | 0.0 | 0.0 | 0.0 |
| Kidney | 0.0 | 0.0 | 0.0 | 0.0 | 0.0 | 0.0 |
| Sm. Intestine | 0.0 | 0.0 | 0.0 | 0.0 | 0.0 | 0.0 |
| Lg. Intestine | 0.0 | 0.0 | 0.0 | 0.0 | 0.0 | 0.0 |
| Stomach | 0.0 | 0.0 | 0.0 | 0.0 | 0.0 | 0.0 |
| Carcass | 0.8 | 0.6 | 1.1 | — | — | — |
| Leg (including injection site) | 98.7 | 98.8 | 98.4 | 97.8 | 97.7 | 98.3 |
| Urine/Feces | 0.5 | 0.6 | 0.5 | 1.2 | 1.5 | 1.5 |

Example 25

Preparation of Composition (Y-90 Coated 5.0 µm Hydroxyapatite Particles—Urease Initiated)

Y-90 was received from Perkin Elmer in a minimal volume of 0.05M HCl. Activity was measured to be about 1.18 mCi using a Capintec CRC-55 dose calibrator. The activity concentration was adjusted to about 40 µCi/µL by the addition of 44 µL of 0.05 M HCl.

2.1 µL of a 50 mg/mL slurry of 5.0 µm hydroxyapatite particles in distilled water was mixed with 209 µL of 8.6 M urea, 10 µL of 0.3 M YCl$_3$ and 777 µL of distilled water in a screw cap micro-centrifuge tube. The solution was mixed for 5 sec using a VWR mini vortexer. With a micropipette, 375 µL was removed and placed in a separate micro-centrifuge tube. 15 µL of the Y-90 solution (prepared above) was added to the new vial. The activity was measured to be 380 µCi. 20 µL of an acetate-buffered, 20 mg/mL urease solution was added to the vial and placed on a nutator for 1 hr with gentle agitation. The vial was then centrifuged for 1.5 min on a setting of 10 RPM. 400 µL of the supernatant was carefully removed with a micropipette. The activity of the removed supernatant was 21.1 µCi. To the original vial, 400 µL of saline solution was added and the vial was mixed with a mini vortexer for 5 min.

The composition of this example is representative of both Formula (I) wherein t, b, c, r and v are all equal to 0, q and a are both equal to 1, and M* is Y-90; and Formula (II) wherein v and r are both equal to 0, q is equal to 1, and M* is Y-90.

Example 26

Composition of Example 25 Administered to Mouse Muscle

Six male BALB/c mice were each injected, housed, sacrificed and assayed in the manner of Example 2 using 20 µL of the Composition prepared according to the procedure of Example 25. The data, shown below in Table 13, indicate the average percent injected dose (% ID) in each tissue/sample.

TABLE 13

Average % Dose Injection (% ID) of Y-90

| | 6 days | 8 days | 11 days |
|---|---|---|---|
| Blood | 0.0 | 0.0 | 0.0 |
| Heart | 0.0 | 0.0 | 0.0 |
| Lung | 0.0 | 0.0 | 0.0 |
| Left Femur | 0.0 | 0.0 | 0.0 |
| Left Thigh | 0.0 | 0.0 | 0.0 |
| Liver | 0.0 | 0.0 | 0.0 |
| Spleen | 0.0 | 0.0 | 0.0 |
| Kidney | 0.0 | 0.0 | 0.0 |
| Small Intestine | 0.0 | 0.0 | 0.0 |
| Large Intestine | 0.0 | 0.0 | 0.0 |
| Stomach | 0.0 | 0.0 | 0.0 |
| Carcass | 0.3 | 0.5 | 0.2 |
| Leg (including injection site) | 99.5 | 99.3 | 99.8 |
| Urine/Feces | 0.2 | 0.3 | 0.0 |

Example 27

Preparation of Composition (Sn-117m, 0.005 M SnCl$_4$, 0.01 M YCl$_3$, 1.4 M Urea Heated 4 Hours)

Sn-117m in 4 N HCl with an activity concentration of about 63.1 mCi in 5 µL. The acid concentration was decreased to about 1.1 M HCl by the addition of 15 µL of 0.05 M HCl.

170 µL of 3 M Urea, 85 µL of 0.04 M YCl$_3$ in 0.05 M HCl, 85 µL of 0.02 M SnCl$_4$ in 0.05 M HCl and 18 µL of Sn-117m (prepared above) were mixed in a screw-cap micro-centrifuge tube. The solution was mixed for 5 sec using a VWR mini vortexer. The vial was then clamped onto a ring stand and lowered into a 100 mL beaker of water at about 90° C. for 4 hr.

The composition of this example is representative of both Formula (I) wherein q, t, a, b and r are all equal to 0, c and p are both equal to 1, and M is Y; and Formula (IV) wherein q and r are both equal to 0, p is equal to 1, and M is Y.

Example 28

Composition of Example 27 Administered to Rat Knee

Four male Sprague Dawley rats were each injected and housed in the manner of Example 2 using 20 µL of the Composition prepared according to the procedure of Example 27. The animals were sacrificed at 13 days (about 1 half-life) and 28 days (about 2 half-lives) in groups of two and assayed in the manner of Example 2. The data, shown below in Table 14, indicate the average percent injected dose in each tissue/sample.

TABLE 14

Average % Injected Dose (% ID) of Sn-117m

| | 13 days | 28 days |
|---|---|---|
| Calculated Blood | 0.0 | 0.0 |
| Heart | 0.0 | 0.0 |
| Lung | 0.0 | 0.0 |
| Calculated Skeleton | 0.4 | 0.6 |

TABLE 14-continued

Average % Injected Dose (% ID) of Sn-117m

|  | 13 days | 28 days |
|---|---|---|
| Calculated Muscle | 0.0 | 0.0 |
| Liver | 0.0 | 0.0 |
| Spleen | 0.0 | 0.0 |
| Kidney | 0.0 | 0.0 |
| Sm. Intestine | 0.0 | 0.0 |
| Lg. Intestine | 0.0 | 0.0 |
| Stomach | 0.0 | 0.0 |
| Leg (injection site) | 98.8 | 98.2 |
| Urine/Feces | 0.8 | 1.2 |

Example 29

Preparation of Composition (Sn-117m, 0.01 M SnCl$_4$, 0.47 M Urea Heated 4 hr)

170 μL of 1 M Urea, 170 μL of 0.02 M SnCl$_4$ in 0.05 M HCl and 18 μL of Sn-117m (prepared in Example 27) were mixed in a screw-cap micro-centrifuge tube. The solution was mixed for 5 seconds using a VWR mini vortexer. The vial was then clamped onto a ring stand and lowered into a 100 mL beaker of water at about 90° C. for 4 hr.

The composition of this example is representative of both Formula (I) wherein q, t, a, b, p and r are all equal to 0, c is equal to 1; and Formula (IV) wherein q, p and r are all equal to 0.

Example 30

Composition of Example 29 Administered to Rat Knee

Three male Sprague Dawley rats were each injected and housed in the manner of Example 2 using 20 μL of the Composition prepared according to the procedure of Example 29. One animal was sacrificed at 13 days (about 1 half-life) and two animals were sacrificed at 28 days (about 2 half-lives) and assayed in the manner of Example 2. The data, shown below in Table 15, indicate the average percent injected dose in each tissue/sample.

TABLE 15

Average % Injected Dose (% ID) of Sn-117m

|  | 13 days | 28 days |
|---|---|---|
| Calculated Blood | 0.0 | 0.0 |
| Heart | 0.0 | 0.0 |
| Lung | 0.0 | 0.0 |
| Calculated Skeleton | 0.0 | 0.0 |
| Calculated Muscle | 0.0 | 0.0 |
| Liver | 0.0 | 0.0 |
| Spleen | 0.0 | 0.0 |
| Kidney | 0.0 | 0.0 |
| Sm. Intestine | 0.0 | 0.0 |
| Lg. Intestine | 0.0 | 0.0 |
| Stomach | 0.0 | 0.0 |
| Leg (injection site) | 99.9 | 99.9 |
| Urine/Feces | 0.1 | 0.1 |

Example 31

Preparation of Composition (Sn-117m, 0.004 M SnCl$_4$, 0.036 M FeCl$_3$, 2.25M Urea Heated 2 hr)

50 μL of 5 M Urea, 12 μL of 0.04 M SnCl$_4$ in 0.05 M HCl, 25 μL of 0.16 M FeCl$_3$ in 0.05 M HCl, 13 μL of DI water and 11 μL of Sn-117m (21.9 μCi) were mixed in a 1.5 mL screw-cap micro-centrifuge tube. The solution was mixed for 5 sec using a VWR mini vortexer. The vial was then clamped onto a ring stand and lowered into a 100 mL beaker of water at about 90° C. for 2 hr. The final pH was 6.5-7.

The composition of this example is representative of both Formula (I) wherein q, a, b, p and r are all equal to 0, t and c are both equal to 1; and Formula (V) wherein p is equal to 0.

Example 32

Composition of Example 31 Administered to Rat Knee

One male Sprague Dawley rat was injected and housed in the manner of Example 2 using 20 μL of the Composition prepared according to the procedure of Example 31. The animal was sacrificed at 4 days and assayed in the manner of Example 2. The data, shown below in Table 16, indicate the average percent injected dose in each tissue/sample.

TABLE 16

Average % Injected Dose (% ID) of Sn-117m

|  | 4 days |
|---|---|
| Calculated Blood | 0.0 |
| Heart | 0.0 |
| Lung | 0.0 |
| Calculated Skeleton | 0.3 |
| Calculated Muscle | 0.1 |
| Liver | 0.0 |
| Spleen | 0.0 |
| Kidney | 0.0 |
| Sm. Intestine | 0.0 |
| Lg. Intestine | 0.0 |
| Stomach | 0.0 |
| Leg (injection site) | 99.2 |
| Urine/Feces | 0.4 |

Example 33

Preparation of Composition (Y-90, 0.24 M Urea, 0.005 M YCl$_3$ Heated 1.5 hr)

Y-90 was received from Perkin Elmer as yttrium chloride in a minimal volume of 0.05 M HCl. Activity was stated to be about 40 mCi.

95 μL of 0.5 M urea was mixed with 95 μL of 0.01 M YCl$_3$ and 10 μL of the Y-90 solution in a small screw-cap conical micro-centrifuge tube. The activity was measured to be 30 mCi using a dose calibrator. The vial was then clamped onto a ring stand and lowered into a 500 mL beaker of boiling water for 1.5 hr.

To this was then added 5 μL of 0.2% erioglaucine (1-D&C Blue #1) to color the solution for ease of visualization while dispensing.

The composition of this example is representative of both Formula (I) wherein q, t, b, c, r and v are all equal to 0, a is equal to 1, and M* is Y-90; and Formula (II) wherein q, v and r are all equal to 0, and M* is Y-90.

Example 34

Treatment of Canine Osteosarcoma

A 147 lb. (67 kg) male St. Bernard, 4 years old, was presented in pain and limping. X-ray examination of the right distal radius indicated a tumor of approximately 90 cc in volume. The tumor was diagnosed via biopsy as being a Grade I or II osteosarcoma. Chest radiographs indicated no evidence of metastases to the lungs.

On the day of treatment, the dog was anesthetized and the area of the distal radius shaved. The osteosarcoma was easily discernible.

Using custom-made three piece adapters (hypodermic, cortex, stylet) and micro bone drill (Valco Instruments Company), a total of 38, 0.45 mm holes, 1 cm apart, 1-3 cm deep were drilled into the tumor. The hypodermic adapter anchors to bone and becomes the guide for the wire drill bit, the cortex adapter slides through the hypodermic adapter and extends into the hole drilled to avoid locational loss, the stylet adapter slides through the cortex adapter to prevent loss of body fluids and coagulation.

One at a time using a 10 µL syringe, the Y-90 composition prepared according to the procedure of Example 33 was injected into the tumor through each cortex adapter after removal of the stylet adapter. Depending upon the depth of the hole, 1, 2 or 3 injections of 1.5 µL (ca. 200 µCO were made such that the 1 cm spacing was maintained. A total of 117 µL (ca. 17 mCi) was injected into the tumor. Dosimetry calculations indicated that this quantity of composition, spaced as indicated, delivered a minimum of 50 Gy to the entire tumor mass. The adapters were removed immediately after injection.

Scanning with a survey meter indicated all of the activity was localized in the tumor.

The day following treatment, the dog was walking without a limp. As of the most recent examination (1½ months post treatment) blood work (CBC) and radiographs indicated no evidence of myelosuppression and no evidence of metastases. It is the opinion of independent clinicians as well as the owner of the dog that this treatment had a positive effect on the dog's quality of life, they are pleased with progress to date and no side effects have been noted. Other observations include no loss of appetite and continued pain relief without the need for pain medication.

Example A (Comparative)

Preparation of Composition (Y-90, Saline)

Y-90 was received from Perkin Elmer as yttrium chloride in a minimal volume of 0.05M HCl. The activity concentration was adjusted to about 200 µCi/µL by the addition of 11 µL of 0.05 M HCl to 1 µL of Y-90. Activity was measured to be 2500 µCi using a Capintec CRC-55 dose calibrator.

420 µL of saline was mixed with 4 µL of the Y-90 solution (prepared above) in a small screw cap conical micro-centrifuge tube. The solution was mixed for 5 sec using a VWR mini vortexer. The pH before drawing doses for injection was approximately 4.7.

Example B (Comparative)

Administering Composition of Example A to Mouse Muscle and Rat Knee

Six male BALB/c mice and six male Sprague Dawley rats were each injected, housed, sacrificed and assayed in the manner of Example 2 using 20 µL of the Composition prepared according to the procedure of Example A. The data, shown below in Table 17, indicate the average percent injected dose (% ID) in each tissue/sample.

TABLE 17

Average % Injected Dose (% ID) of Y-90

| | Mice | | | Rats | | |
|---|---|---|---|---|---|---|
| | 6 days | 8 days | 11 days | 6 days | 8 days | 11 days |
| Blood | 0.0 | 0.0 | 0.0 | — | — | — |
| Calculated Blood | — | — | — | 0.0 | 0.0 | 0.0 |
| Heart | 0.1 | 0.2 | 0.0 | 0.0 | 0.0 | 0.0 |
| Lung | 0.0 | 0.1 | 0.1 | 0.1 | 0.1 | 0.0 |
| Left Femur | 1.7 | 2.2 | 2.7 | — | — | — |
| Calculated Skeleton | — | — | — | 42.9 | 37.6 | 48.0 |
| Left Thigh | 0.0 | 0.0 | 0.0 | — | — | — |
| Calculated Muscle | — | — | — | 0.0 | 0.0 | 0.0 |
| Liver | 2.6 | 2.0 | 1.7 | 0.9 | 0.8 | 0.3 |
| Spleen | 0.1 | 0.1 | 0.1 | 0.1 | 0.0 | 0.0 |
| Kidney | 1.7 | 1.7 | 1.7 | 0.9 | 0.6 | 0.6 |
| Sm. Intestine | 0.3 | 0.2 | 0.2 | 0.2 | 0.2 | 0.1 |
| Lg. Intestine | 0.1 | 0.1 | 0.1 | 0.1 | 0.1 | 0.0 |
| Stomach | 0.1 | 0.1 | 0.1 | 0.2 | 0.3 | 0.1 |
| Carcass | 40.7 | 47.9 | 51.3 | — | — | — |
| Leg (including injection site) | 10.2 | 10.0 | 13.7 | 29.6 | 32.2 | 26.9 |
| Urine/Feces | 42.4 | 35.4 | 28.2 | 24.9 | 28.1 | 23.9 |

Example C (Comparative)

Preparation of Composition (Y-90, 1 M NaOH)

Y-90 was received from Perkin Elmer as yttrium chloride in a minimal volume of 0.05M HCl. The activity was measured to be about 10 mCi using a Capintec CRC-55 dose calibrator. The activity concentration was adjusted to about 50 µCi/µL by the addition of 0.05 M HCl.

190 µL of 1 M NaOH was mixed with 10 µL of the Y-90 (prepared above) in a small screw cap conical micro-centrifuge tube. The solution was mixed for 5 sec using a VWR mini vortexer.

Example D (Comparative)

Administering Composition of Example C to Mouse Muscle and Rat Knee

Six male BALB/c mice and six male Sprague Dawley rats were each injected, housed, sacrificed and assayed in the manner of Example 2 using 20 µL of the Composition prepared according to the procedure of Example C. The data, shown below in Table 18, indicate the average percent injected dose (% ID) in each tissue/sample.

TABLE 18

Average % Injected Dose (% ID) of Y-90

| | Mice | | | Rats | | |
|---|---|---|---|---|---|---|
| | 6 days | 8 days | 11 days | 6 days | 8 days | 11 days |
| Blood | 0.0 | 0.0 | 0.1 | — | — | — |
| Calculated Blood | — | — | — | 0.0 | 0.0 | 0.0 |
| Heart | 0.0 | 0.0 | 0.1 | 0.0 | 0.0 | 0.0 |
| Lung | 0.0 | 0.0 | 0.1 | 0.0 | 0.0 | 0.0 |
| Left Femur | 0.2 | 0.2 | 0.4 | — | — | — |
| Calculated | — | — | — | 4.9 | 5.1 | 7.8 |

TABLE 18-continued

| | Average % Injected Dose (% ID) of Y-90 | | | | | |
|---|---|---|---|---|---|---|
| | Mice | | | Rats | | |
| | 6 days | 8 days | 11 days | 6 days | 8 days | 11 days |
| Skeleton | | | | | | |
| Left Thigh | 0.0 | 0.0 | 0.1 | — | — | — |
| Calculated Muscle | — | — | — | 0.0 | 0.0 | 0.0 |
| Liver | 0.2 | 0.3 | 0.4 | 0.3 | 0.2 | 0.3 |
| Spleen | 0.0 | 0.0 | 0.1 | 0.0 | 0.0 | 0.0 |
| Kidney | 0.2 | 0.2 | 0.4 | 0.2 | 0.1 | 0.1 |
| Sm. Intestine | 0.0 | 0.0 | 0.2 | 0.0 | 0.0 | 0.0 |
| Lg. Intestine | 0.0 | 0.0 | 0.1 | 0.0 | 0.0 | 0.0 |
| Stomach | 0.0 | 0.0 | 0.2 | 0.0 | 0.0 | 0.0 |
| Carcass | 4.1 | 7.8 | 6.2 | — | — | — |
| Leg (including injection site) | 92.0 | 87.5 | 85.9 | 91.7 | 90.8 | 84.7 |
| Urine/Feces | 3.2 | 3.9 | 5.5 | 2.9 | 3.8 | 7.2 |

Example E (Comparative)

Preparation of Composition (Y-90, 1 M $Na_2CO_3$)

Y-90 was received from Perkin Elmer as yttrium chloride in a minimal volume of 0.05M HCl. The activity was measured to be about 10 mCi using a Capintec CRC-55 dose calibrator. The activity concentration was adjusted to about 50 µCi/µL by the addition of 0.05 M HCl.

190 µL of 1 M $Na_2CO_3$ was mixed with 10 µL of the Y-90 (prepared above) in a small screw cap conical micro-centrifuge tube. The solution was mixed for 5 sec using a VWR mini vortexer.

Example F (Comparative)

Administering Composition of Example C to Mouse Muscle and Rat Knee

Six male BALB/c mice and six male Sprague Dawley rats were each injected, housed, sacrificed and assayed in the manner of Example 2 using 20 µL of the Composition prepared according to the procedure of Example E. The data, shown below in Table 19, indicate the average percent injected dose (% ID) in each tissue/sample.

TABLE 19

| | Average % Injected Dose (% ID) of Y-90 | | | | | |
|---|---|---|---|---|---|---|
| | Mice | | | Rats | | |
| | 6 days | 8 days | 11 days | 6 days | 8 days | 11 days |
| Blood | 0.0 | 0.0 | 0.1 | — | — | — |
| Calculated Blood | — | — | — | 0.0 | 0.0 | 0.0 |
| Heart | 0.0 | 0.0 | 0.1 | 0.0 | 0.0 | 0.0 |
| Lung | 0.0 | 0.0 | 0.1 | 0.0 | 0.0 | 0.0 |
| Left Femur | 0.3 | 0.7 | 0.9 | — | — | — |
| Calculated Skeleton | — | — | — | 16.0 | 16.8 | 20.9 |
| Left Thigh | 0.0 | 0.0 | 0.1 | — | — | — |
| Calculated Muscle | — | — | — | 0.0 | 0.0 | 0.0 |
| Liver | 0.5 | 1.2 | 0.9 | 3.2 | 1.2 | 1.3 |
| Spleen | 0.0 | 0.1 | 0.1 | 0.4 | 0.2 | 0.1 |
| Kidney | 0.5 | 0.6 | 0.7 | 0.5 | 0.4 | 0.6 |

TABLE 19-continued

| | Average % Injected Dose (% ID) of Y-90 | | | | | |
|---|---|---|---|---|---|---|
| | Mice | | | Rats | | |
| | 6 days | 8 days | 11 days | 6 days | 8 days | 11 days |
| Sm. Intestine | 0.1 | 0.1 | 0.2 | 0.1 | 0.1 | 0.1 |
| Lg. Intestine | 0.0 | 0.0 | 0.1 | 0.1 | 0.1 | 0.0 |
| Stomach | 0.0 | 0.1 | 0.1 | 0.2 | 0.1 | 0.1 |
| Carcass | 8.3 | 15.7 | 15.8 | — | — | — |
| Leg (including injection site) | 83.5 | 71.6 | 70.7 | 69.0 | 70.2 | 60.5 |
| Urine/Feces | 6.7 | 9.8 | 10.1 | 10.6 | 10.9 | 16.4 |

Example G (Comparative)

Ho-166 Chloride

Ho-166 in 0.1M HCl was obtained from MURR. The pH was measured with pH paper showing a pH of about 1. A miniature drill was used to create a hole in the femur of an anesthetized Sprague Dawley rat. A miniature pump was used to deliver 3 µL of Ho-166 solution into the hole created by the drill. Two hours after the injection of the dose the rat was sacrificed and dissected. The amount of activity found in the site of injection was 5% of the injected dose. 52% of the dose was found in the liver and 23% of the dose was found in the rest of the bone.

Example H (Comparative)

Preparation of Composition (Sm-153-DOTMP)

Sm-153 in 0.1 M HCl was obtained from MURR. The complex formed between Sm-153 and DOTMP was prepared by combining 5 µL of Sm-153 with 5.6 µL of a solution containing 13 mg/mL of DOTMP (previously adjusted to pH 7-8) and 4 µL of water. An additional 5 µL of DOTMP solution was added to obtain high complex yields. The amount of Sm found as a complex was 99% by ion exchange chromatography. DOTMP was prepared and purified by known synthetic techniques. The chelant was greater than 99% pure.

A miniature drill was used to create a hole in the femur of an anesthetized Sprague Dawley rat. A miniature pump was used to deliver 2 µL of Sm-153-DOTMP solution into the hole created by the drill. Two hours after the injection of the dose the rat was sacrificed and dissected. The amount of activity found in the site of injection was 9% of the injected dose and about 20% was found in the rest of the bone. An average of 65% of the injected dose was found in the urine.

Example I (Comparative)

Preparation of Composition (Ho-166, 1 M NaOH, $FeCl_3$ and Administration to Mouse Muscle)

Ho-166 was received from MURR as holmium chloride in 850 µL of 0.05 M HCl. The activity was measured to be 1 mCi using a Capintec CRC dose calibrator. To increase the dose concentration, the solution was placed in a heating block at about 90° C. to evaporate the excess liquid. After 40 min, the solution was removed from heat and 50 µL was removed and placed in a small screw cap conical micro-centrifuge tube. The activity of the measured aliquot was 800 μCi. The final activity was 16 μCi per μL.

FeCl₃ solution was prepared by dissolving 0.0956 grams of FeCl₃.6H₂O in 20 milliliters of distilled water. 27 μL of the H0-166 solution prepared above was mixed with 500 μL of the FeCl₃ solution and placed in a small screw cap conical micro-centrifuge tube. 30 μL of 1 N NaOH solution was added with mixing and the reaction mixture was then agitated for 5 sec using a VWR mini-vortexer.

Two male BALB/c mice were each injected and housed in the manner of Example 2 using 20 μL of the present Composition. The animals were sacrificed at 3 days and assayed in the manner of Example 2. Approximately 95.6% of the dose was found at the site of injection. However, 3.3% was found in the carcass (the carcass consists of the remaining musculoskeletal structure, reproductive organs, the skin, head, limbs and tail), 0.7% in the liver, 0.3% in the urine/feces, and 0.1% in the kidneys.

Example J (Comparative)

Preparation of Composition (Y-90, 1 M NaOH, FeCl₃) and Administration to Mouse Muscle Y-90 was received from Perkin Elmer as yttrium chloride in a minimal volume of 0.05 M HCl. The activity was adjusted to about 200 μCi/μL by the addition of 11 μL of 0.05 M HCl to 1μL of Y-90. Activity was measured to be 2500 μCi using a Capintec CRC dose calibrator.

FeCl₃ solution was prepared by dissolving 0.0956 grams of FeCl₃.6 H₂O in 20 milliliters of distilled water. 27 μL of the Y-90 solution prepared above was mixed with 500 μL of the FeCl₃ solution and placed in a small screw cap conical micro-centrifuge tube. 30 μL of 1 N NaOH solution was added with mixing and the reaction mixture was then agitated for 5 sec with a VWR mini-vortexer. An additional purification step was then performed which consisted in placing the micro-centrifuge tube in an Eppendorf micro-centrifuge for 5 min at 1600 RPM. After centrifuging, 450 μL of the supernatant was carefully removed and placed in a separate vial. The activity of the supernatant was 24 μCI. 450 μL of saline was added to the original vial and was mixed for 5 sec using a mini vortexer.

Two male BALB/c mice were each injected and housed in the manner of Example 2 using 20 μL of the present Composition. The animals were sacrificed at 11 days and assayed in the manner of Example 2. Approximately 94.7% of the dose was found at the site of injection. However, 3.5% was found in the carcass (the carcass consists of the remaining musculoskeletal structure, reproductive organs, the skin, head, limbs and tail), 1.4% in the urine/feces, 0.1% in the liver, 0.1% in the kidneys, and 0.1% in the left femur.

Example K (Comparative)

Preparation of Composition (Sn-117m-DTPA)

342 μL of a 50 mM diethylenetriaminepentaacetic acid (DTPA) solution was mixed in a screw-cap micro-centrifuge tube with 20 μL of Sn-117m solution (prepared according to the procedure of Example 27). The vial was placed on a rotational platform overnight. The solution was mixed for 5 sec using a VWR mini vortexer. The complex yield was determined to be 94% using a cation exchange column (SP Sephadex C-25, Sigma Aldrich).

Example L (Comparative)

Composition of Example K Administered to Rat Knee

Three male Sprague Dawley rats were each injected and housed in the manner of Example 2 using 20 μL of the Composition prepared according to the procedure of Example K. One animal was sacrificed at 14 days (about 1 half-life) and two animals were sacrificed at 28 days (about 2 half-lives) and assayed in the manner of Example 2. The data, shown below in Table 20, indicate the average percent injected dose in each tissue/sample.

TABLE 20

| Average % Injected Dose (% ID) of Sn-117m | | |
|---|---|---|
| | 14 days | 28 days |
| Calculated Blood | 0.0 | 0.0 |
| Heart | 0.0 | 0.0 |
| Lung | 0.0 | 0.0 |
| Calculated Skeleton | 28.0 | 30.0 |
| Calculated Muscle | 0.3 | 0.1 |
| Liver | 0.4 | 0.4 |
| Spleen | 0.0 | 0.0 |
| Kidney | 0.4 | 0.3 |
| Sm. Intestine | 0.0 | 0.0 |
| Lg. Intestine | 0.0 | 0.0 |
| Stomach | 0.0 | 0.0 |
| Leg (injection site) | 31.2 | 22.6 |
| Urine/Feces | 39.5 | 46.6 |

Example M (Comparative)

Preparation of Composition (Sn-117m-Citrate)

Sn-117m in 4 N HCl with an activity concentration of about 77 mCi in 10 μL was mixed with 190 μL 0.1 M citric acid. The pH was 1-2. The pH was adjusted from the initial 1-2 to 6-7 using NH₄OH and NaOH.

Example N (Comparative)

Composition of Example M Administered to Rat Knee

Two male Sprague Dawley rats were each injected and housed in the manner of Example 2 using 20 μL of the Composition prepared according to the procedure of Example M. The animals were sacrificed at 14 days (about 1 half-life) and assayed in the manner of Example 2. The data, shown below in Table 21, indicate the average percent injected dose in each tissue/sample.

TABLE 21

| Average % Injected Dose (% ID) of Sn-117m | |
|---|---|
| | 14 days |
| Calculated Blood | 0.0 |
| Heart | 0.0 |
| Lung | 0.0 |
| Calculated Skeleton | 22.8 |
| Calculated Muscle | 0.7 |
| Liver | 0.3 |
| Spleen | 0.0 |
| Kidney | 0.7 |
| Sm. Intestine | 0.1 |

TABLE 21-continued

| Average % Injected Dose (% ID) of Sn-117m | |
|---|---|
| | 14 days |
| Lg. Intestine | 0.1 |
| Stomach | 0.0 |
| Leg (injection site) | 15.5 |
| Urine/Feces | 59.6 |

Example O (Comparative)

Preparation of Composition (Sn(II)-117m, 0.01 M SnCl$_4$, 0.45 M Urea Heated 4 hr)

Stannous [Sn(II)] Sn-117m was obtained from Brookhaven National Laboratory with an activity concentration of 2 µCi/µL. 35 µL of this Sn(II)-117m was combined with 170 µL of 1 M Urea, 170 µL of 0.02 M SnCl$_4$ in 0.05 M HCl in a screw-cap micro-centrifuge tube. The solution was mixed for 5 sec using a VWR mini vortexer. The vial was then clamped onto a ring stand and lowered into a 100 mL beaker of water at about 90° C. for 4 hr.

Example P (Comparative)

Composition of Example O Administered to Rat Knee

Four male Sprague Dawley rats were each injected and housed in the manner of Example 2 using 20 µL of the Composition prepared according to the procedure of Example 0. The animals were sacrificed at 14 days (about 1 half-life) and at 28 days (about 2 half-lives) and assayed in the manner of Example 2. The data, shown below in Table 22, indicate the average percent injected dose in each tissue/sample.

TABLE 22

| Average % Injected Dose (% ID) of Sn-117m | | |
|---|---|---|
| | 14 days | 28 days |
| Calculated Blood | 0.0 | 0.0 |
| Heart | 0.0 | 0.0 |
| Lung | 0.0 | 0.0 |
| Calculated Skeleton | 22.4 | 22.4 |
| Calculated Muscle | 0.1 | 0.0 |
| Liver | 0.5 | 0.3 |
| Spleen | 0.0 | 0.0 |
| Kidney | 0.4 | 0.3 |
| Sm. Intestine | 0.1 | 0.0 |
| Lg. Intestine | 0.2 | 0.0 |
| Stomach | 0.0 | 0.0 |
| Leg (injection site) | 48.6 | 36.3 |
| Urine/Feces | 27.7 | 40.6 |

Example Q (Comparative)

Preparation of Composition (Sn-117m, 0.02 M SnCl$_4$, 1 M NaOH)

Sn-117m in 4 N HCl was assayed to have an activity concentration of 5.1 µCi/µL. 18 µL of this Sn-117m was combined with 170 µL of 0.02 M SnCl$_4$ in 0.05 N HCl in a small screw cap conical micro-centrifuge tube. To this was added 100 µL of 1 M NaOH. The solution was mixed for 5 sec using a VWR mini vortexer.

Example R (Comparative)

Composition of Example Q Administered to Rat Knee

Two male Sprague Dawley rats were each injected and housed in the manner of Example 2 using 20 µL of the Composition prepared according to the procedure of Example Q. The animals were sacrificed at 7 days and assayed in the manner of Example 2. The data, shown below in Table 23, indicate the average percent injected dose in each tissue/sample.

TABLE 23

| Average % Injected Dose (% ID) of Sn-117m | |
|---|---|
| | 7 days |
| Calculated Blood | 0.1 |
| Heart | 0.0 |
| Lung | 0.0 |
| Calculated Skeleton | 6.5 |
| Calculated Muscle | 0.8 |
| Liver | 0.2 |
| Spleen | 0.0 |
| Kidney | 0.6 |
| Sm. Intestine | 0.0 |
| Lg. Intestine | 0.0 |
| Stomach | 0.0 |
| Leg (injection site) | 74.5 |
| Urine/Feces | 17.1 |

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A composition comprising a Non-Sealed, radioactive pharmaceutically-acceptable composition of the formula

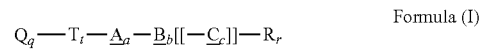

Formula (I)

$$Q_q\text{---}T_t\text{---}\underline{A}_a\text{---}\underline{B}_b[[\text{---}\underline{C}_c]]\text{---}R_r$$

wherein:
Q is a Substrate of a different material from $\underline{A}_a$-$\underline{B}_b$ entity, wherein such Substrate has the $\underline{A}_a$-$\underline{B}_b$ entity deposited or adhered thereto; and is an injectable or implantable Substrate that is either pharmaceutically-acceptable or can be Coated to be pharmaceutically-acceptable;
q is equal to 1 or 0, wherein 1 means the entity is present and 0 means the entity is not present;
T is a non-radioactive iron hydroxide, iron oxide, gadolinium hydroxide or gadolinium oxide;
t is equal to 1 or 0, wherein 1 means the entity is present and 0 means the entity is not present,
$\underline{A}$ is $J_vM^*_w(OH)_x(CO_3)_y(AN)_z\cdot nH_2O$, wherein:
J is lanthanide metal ion capable of forming hydroxy carbonate compounds;
v is greater than or equal to 0;
M* is radioactive Sm-153, Ho-166, Y-90, or Lu-177 or mixtures thereof, wherein their respective non-radioactive Rare-earth Type Metal is usually present;
w, x and y are each independently greater than 0;

AN is a pharmaceutically-acceptable anionic moiety; and z and n are each independently greater than or equal, to 0;

a is equal to 1 or 0, wherein 1 means the entity is present and 0 means the entity is not present;

B is $M^*_w(OH)_x(CO_3)_y \cdot nH_2O$, wherein:
M* is radioactive Sm-153, Ho-166, Y-90, or Lu-177 or mixtures thereof, wherein their respective non-radioactive Rare-earth Type Metal is usually present;
w, x and y are each independently greater than 0; and n is greater than or equal to 0;

b is equal to 1 or 0, wherein 1 means the entity is present and 0 means the entity is not present;

R is a Coat comprising a substance of a different composition than $\underline{A}_a\text{-}\underline{B}_b$ entity, which covers $\underline{A}\text{-}\underline{B}_b$, and if q is 1, also Coats Substrate Q, and the resulting Coated composition is pharmaceutically-acceptable for injection; and r is equal to 1 or 0, wherein 1 means the entity is present and 0 means the entity is not present;

with the provisos that one and only one of a and b are equal to 1, the other being equal to 0; if either q or t is equal to 1, then the other is equal to 0; each of v, w, x, y and z are of a numeric value, fractional values included, such that electrical neutrality is attained; and n is greater than or equal to 0 to provide optional water of hydration.

2. The composition of claim 1, wherein in Formula (I) a is equal to 1; and t, b and c are equal to 0; and is represented by the formula:

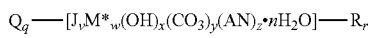

Formula (II)

wherein:
Q, J, M*, AN, R, q, v, w, x, z and n are as defined as for Formula (I) in claim 1.

3. The composition of claim 1, wherein in Formula (I) t and b are equal to 1; and q, a, c and r are each equal to 0, and is represented by the formula;

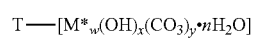

Formula (III)

wherein:
T, M*, w, x, y and n are as defined for Formula (I) in claim 1.

4. The composition of claim 2, wherein the compound of Formula (II) has q, v, and r all equal to 0.

5. The composition of claim 2, wherein the compound of Formula (II) has q equal to 1; and v and r both equal to 0.

6. The composition of claim 1, wherein Q is alumina, silica, barium titanate, metal oxides and hydroxides, polystyrene latex, hydroxyapatite, magnetic particles, polystyrene-polymethaetyl ate copolymers, poly(lactic acid) particles, DL-lactide/glycolidc copolymers, stents, shunts, or various derivatives of these particles containing surface modifications.

7. The composition of claim 1, wherein the lanthanide metal ion of J is fluorescent gadolinium, europium, or erbium.

8. The composition of claim 1, wherein AN is nitrate, chloride, sulfate, hydrogen phosphate, dihydrogen phosphate, fluoride, or oxalate.

9. A pharmaceutically-acceptable formulation of the composition of Formula (I) which is that of Formula (II) or Formula (III) as defined in claim 2 or claim 3, respectively, comprising a pharmaceutically-acceptable liquid suitable for injection.

10. The formulation of claim 9, further comprising one or more pharmaceutically-acceptable carriers, excipients, diluents, suspension aids, preservatives, crystal growth modifiers or buffers.

11. The composition of claim 2, wherein the compound of Formula (II) has q and r all equal to 0.

* * * * *